United States Patent [19]
O'Neill et al.

[11] Patent Number: 5,907,082
[45] Date of Patent: May 25, 1999

[54] OVULE-SPECIFIC GENE EXPRESSION

[75] Inventors: Sharman O'Neill, Davis, Calif.; Jeanette Nadeau, Columbus, Ohio

[73] Assignee: The Regents of the University of California, Oakland, Calif.

[21] Appl. No.: 08/560,398

[22] Filed: Nov. 17, 1995

[51] Int. Cl.⁶ .............................. A01H 5/00; C12N 15/82; C07H 21/04
[52] U.S. Cl. ...................... 800/205; 536/23.6; 536/24.5
[58] Field of Search ........................... 800/205; 536/23.6, 536/24.5

[56] References Cited

PUBLICATIONS

Hake, Sarah (1992) "Unraveling the knots in plant development", *TIG* 8(3):109–114.
Vollbrecht, Erik, et al. (1991) "The developmental gene Knotted-1 is a member of a maize homeobox gene family", *Nature* 350:241–243.
Matsuoka, Makoto, et al. (1993) "Expression of a Rice Homeobox Gene Causes Altered Morphology of Transgenic Plants", *The Plant Cell*, 5:1039–1048.
Ma, Hongchang, et al. (1994) "Identification of a homeobox-containing gene with enhanced expression during soybean (*Glycine max* L.) somatic embryo development", *Plant Molecular Biology* 24:465–473.
Robinson–Beers, Kay, et al. (1992) "Ovule Development in Wild–Type Arabidopsis and Two Female–Sterile Mutants", *The Plant Cell* 4:1237–1249.
Reiser, Lenore, et al. (1993) "The Ovule and the Embryo Sac", *The Plant Cell* 5:1291–1301.
Modrusan, Zora, et al. (1994) "Homeotic Transformation of Ovules into Carpel–like Structures in Arabidopsis", *The Plant Cell* 6:333–349.
Léon–Kloosterziel, Karen M., et al. (1994) "A Seed Shape Mutant of Arabidopsis That is Affected in Integument Development", *The Plant Cell* 6:385–392.
Gaiser, J. Christopher, et al. (1995) "The Arabidopsis Superman Gene Mediates Asymmetric Growth of the Outer Integument of Ovules", *The Plant Cell* 7:333–345.
Ruberti, Ida, et al. (1991) "A novel class of plant proteins containing a homeodomain with a closely linked leucine zipper motif", *The EMBO Journal* 10(7):1787–1791.

Schena, Mark, et al. (1992) "HD–Zip proteins: Members of an Arabidopsis homeodomain protein superfamily", *Proc. Natl. Acad. Sci USA* 89:3894–3898.
Mitsuhashi, Wataru, et al. (1989) "Synthesis and Postranslational Activation of Sulfhydryl–Endopeptidase in Cotyledons of Germinating *Vigna mungo* Seeds", *Plant Physiol.* 89:274–279.
Kalinski, Andrzej, et al. (1990) "Molecular Cloning of a Protein Associated with Soybean Seed Oil Bodies That is Similar to Thiol Proteases of the Papain Family", *The Journal of Biological Chemistry* 265(23): 13843–13848.
Tanaka, Tetsutaro, et al. (1991) "Nucleotide sequence of cDNA for an endopeptidase (EP–C1) from pods of maturing *Phaseolus vulgaris* fruits", *Plant Molecular Biology* 16:1083–1084.
Rogers, John C., et al. (1985) "Aleurain: A barley thiol protease closely related to mammalian cathepsin H", *Proc. Natl. Acad. Sci USA* 82:6512–6516.
Cohen, Larry W., et al. (1986) "Cloning and sequencing of papain–encoding cDNA", *Gene* 48:219–227.
Praekelt, Uta M., et al. (1988) "Molecular analysis of actinidin, the cysteine proteinase of *Actinidia chinensis*".
Nebert, Daniel W., et al. (1987) "P450 Genes: Structure, Evolution, and Regulation", *Ann. Rev. Biochem.* 56:945–993.
Rerie et al. The GLABRA2 gene encodes a homeo domain protein required for normal trichome development in Arabidopsis. Genes & Development. 8:1388–1399, Jun. 1994.
Smith et al. Antisense RNA inhibition of polygalacturonase gene expression in transgenic tomatoes. Nature. 334:724–726, 1988.
Napoli et al. Introduction of a chimeric chalcone synthase gene into petunia results in reversible co–suppression of homologous genes in trans. The Plant Cell. 2:279–289, 1990.

*Primary Examiner*—Douglas W. Robinson
*Assistant Examiner*—Thanda Wai
*Attorney, Agent, or Firm*—Townsend and Townsend and Crew

[57] ABSTRACT

The present invention provides nucleic acid sequences from ovule-specific genes. The nucleic acids are useful in targeting gene expression to ovules or in modulating ovule development.

22 Claims, 1 Drawing Sheet

OVULE-SPECIFIC GENE EXPRESSION

FIELD OF THE INVENTION

The present invention is directed to plant genetic engineering. In particular, it relates to new ovule-specific genes useful in improving agronomically important plants.

BACKGROUND OF THE INVENTION

The angiosperm ovule plays a central role in producing and sheltering the female gametophyte which ultimately gives rise to the egg cell in plant sexual reproduction (Bouman, In *Embryology of Angiosperms*, B. M. Johri, eds (Berlin, Germany: Springer-Verlag), pp. 123–157 (1984)). Additionally, the final product of the ovule, the seed, is a highly significant human food source as well as a common means of propagation of species in which other plant organs are agriculturally important.

As a result of its importance, there is a wealth of descriptive knowledge concerning ovule anatomy and morphology (see, e.g., Huang and Russell, *Int. Rev. Cytol.* 140:233–293 (1992)), though little is known about the molecular basis of ovule development and function. The relative inaccessibility of the ovule within the ovary, as well as the difficulty in harvesting adequate amounts of tissue at known developmental stages, has impeded progress in understanding the molecular basis of ovule development and function. Recently, however, several groups have taken genetic approaches to dissect the underlying mechanisms involved in ovule development. Several mutations affecting ovule and female gametophyte development have been identified, including bel1, sin1, ovm2 and ovm3, which cause female sterility in *Arabidopsis* (Robinson-Beers et al., *Plant Cell* 4:1237–1249 (1992); Reiser and Fischer, *Plant Cell* 5:1291–1301 (1993); Modrusan et al., *Plant Cell* 6:333–349 (1994)). Other genes recently shown to be involved in ovule development are ats (Léon-Kloosterziel et al., *Plant Cell* 6:385–392 (1994)) and sup (Gaiser et al., *Plant Cell* 7:333–345 (1995)). A few mutations defective in aspects of megasporogenesis have also been identified, such as msg in wheat (Joppa et al., 1987), sy-2 in Solanum (Parrott and Hanneman Jr., *Dun. Genome* 30:536–539 (1988)) and Gf in *Arabidopsis* (Rédei, *Genetics* 51:857–872 (1965)).

In spite of the recent progress in defining the genetic control of ovule development, little progress has been reported in the identification and analysis of genes expressed specifically in the ovule and embryo sac. Characterization of such genes would allow for the genetic engineering plants with a variety of desirable traits. For instance, inhibition of genes associated with ovule development may be used to produce seedless fruit. Alternatively, promoters from ovule specific genes can be used to direct expression of desirable heterologous genes to the ovule. The present invention addresses these and other needs.

SUMMARY OF THE INVENTION

The present invention relates to isolated nucleic acid constructs comprising a polynucleotide sequence from an ovule-specific gene. The polynucleotide sequences of the invention hybridize to clones O39 (SEQ ID No: 1), O108 (SEQ ID No: 5), O126 (SEQ ID No: 7), O141 (SEQ ID No: 9), or A20 (SEQ ID No: 11) under stringent conditions. The invention also provides sequences from genes expressed in pollen tubes. These genes are identified by their ability to hybridize to clone O40 (SEQ ID No: 3) under stringent conditions.

The nucleic acid constructs of the invention may further comprise a promoter operably linked to the polynucleotide sequence. In some embodiments, the polynucleotide sequence is linked to the promoter in an antisense orientation. The constructs may comprise a wide variety of promoter sequences. Where ovule-specific expression is desired, ovule-specific promoters are preferred.

The invention also provides transgenic plants comprising a recombinant expression cassette comprising a plant promoter operably linked to a polynucleotide sequences of the invention. The plant promoter may be a heterologous promoter. If expression of an endogenous gene is desired, the polynucleotide sequence may be linked to the promoter in the sense or the antisense orientation. A useful polynucleotide sequence for this purpose is clone O39 (SEQ ID No: 1).

The invention also provides methods of modulating ovule development in a plant. The method comprise introducing into plant tissue a recombinant expression cassette comprising a plant promoter operably linked to a polynucleotide sequence of the invention. The plant tissue is then regenerated into a whole plant, whereby the regenerated plant transcribes the polynucleotide sequence; and plants having inhibited ovule development are selected. The recombinant expression cassette can be introduced into the plant tissue using a variety of techniques, including Agrobacterium-mediated transformation.

Definitions

The phrase "nucleic acid sequence" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including both monocotyledonous and dicotyledonous plants, as well as certain lower plants such as algae. It includes plants of a variety of ploidy levels, including polyploid, diploid and haploid.

A "heterologous sequence" is one that originates from a foreign species, or, if from the same species, is substantially modified from its original form. For example, a heterologous promoter operably linked to a structural gene is from a species different from that from which the structural gene was derived, or, if from the same species, is substantially modified from its original form.

As used herein an "ovule-specific gene" is a gene that is preferentially expressed during ovule development in a plant. For purposes of this application, ovule development begins with cell divisions within the meristematic region of the placental ridges, which elongate and branch to form finger-like ovule primordia. Ovule development ends with fertilization of the egg cell. Exemplary ovule-specific genes are O39, O108, and O141, isolated from Phalaenopsis are described. An ovule-specific gene from *Arabidopsis*, A20, is also disclosed.

As used herein, a homolog of a particular ovule-specific gene (e.g., SEQ ID No: 1) is a second gene in the same plant type or in a different plant type, which has a polynucleotide sequence of at least 50 contiguous nucleotides which are substantially identical (determined as described below) to a sequence in the first gene. It is believed that, in general, homologs share a common evolutionary past.

A "polynucleotide sequence from" a particular ovule-specific gene is a subsequence or full length polynucleotide sequence of an ovule-specific gene which, when present in a transgenic plant, has the desired effect, for example, inhibiting expression of the endogenous gene. A full length sequence of a particular gene disclosed here may contain about 95%, usually at least about 98% of an entire sequence shown in the Sequence Listing, below.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "polynucleotide sequence from" a particular ovule-specific gene. In addition, the term specifically includes those full length sequences substantially identical (determined as described below) with an gene sequence and that encode proteins that retain the function of the gene product.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BLAST) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

In the present invention, mRNA encoded by ovule-specific genes of the invention can be identified in Northern blots under stringent conditions using cDNAs of the invention. For the purposes of this disclosure, stringent conditions for such RNA-DNA hybridizations are those which include at least one wash in 0.2× SSC at 63° C. for 20 minutes, or equivalent conditions. Genomic DNA or cDNA comprising genes of the invention can be identified using the same cDNAs under stringent conditions, which for purposes of this disclosure, include at least one wash (usually 2) in 0.2× SSC at a temperature of at least about 50° C., usually about 55° C., for 20 minutes, or equivalent conditions.

DESCRIPTION OF THE PREFERRED EMBODIMENT

Figure 1:
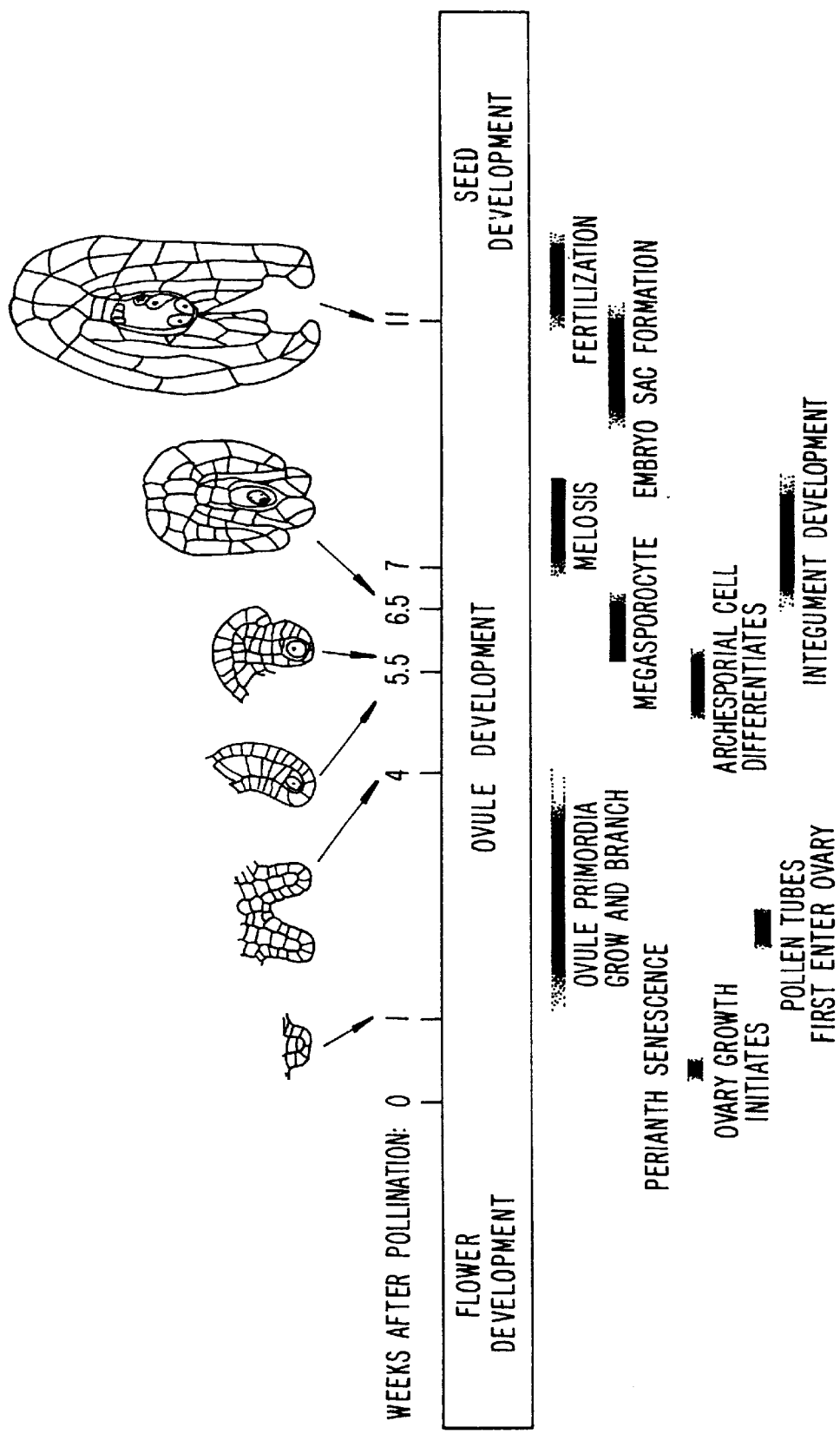
FIG. 1 shows a timeline of Phalaenopsis ovule development. The span of time during which each event takes place is indicated below the timeline.

The present invention provides new ovule-specific genes useful in genetically engineering plants. Promoters from the genes of the invention can be used, for instance, to direct expression of desired heterologous genes in ovules or to control development of ovules (e.g., by inhibiting expression of the gene). In addition, the invention provides a new gene encoding a cytochrome P450 monooxygenase isolated from pollen tubes. Sequences from this gene can be used to modulate expression of cytochrome P450 monooxygenases in a number of plant tissues.

Phalaenopsis ovule development and its regulation following pollination has been described in detail (Zhang and O'Neill *Plant Cell* 5:403–418 (1993)). Although orchid flowers are unusual in that ovule development is delayed until anthesis of the flower and triggered by pollination, once initiated, the processes of megasporogenesis and megagametogenesis are similar to many other plant species with the development of the mature embryo sac being of the Polygonum type. The Polygonum type of embryo sac is found in 70% of all plant species, including Arabidopsis, and is considered to be the prototypical program of embryo sac development (see, e.g., Reiser and Fischer, supra).

The events in ovule development in Phalaenopsis and other plants with Polygonum type embryo sac formation are briefly as follows. The first events are cell divisions within the meristematic region of the placental ridges. These ridges elongate and branch dichotomously several times to form thousands of finger-like ovule primordia. At this stage, cells in the dermal and subdermal layers are densely cytoplasmic. Next, a subdermal cell near the apex of the primordia enlarges to form the archesporial cell. The inner integument initiates as a ring of periclinal cell divisions near the tip of the primordia and the outer integument is initiated shortly thereafter. This is accompanied by asymmetric growth and division of cells on one side of the primordia to establish the anatropous orientation of the ovule. The archesporial cell enlarges further to directly form the megasporocyte which develops a distinctive polar distribution of organelles, enzyme activities and callose within the wall. The nucellus typically remains uniseriate and is crushed between the integuments and megagametophyte at maturity. Following meiosis of the megasporocyte, four products of meiosis are generally formed (only three are formed in some cases) and all but the spore closest to the chalaza degenerate and are crushed by the expanding megaspore. Vacuoles begin to coalesce in the surviving megaspore, and subsequent mitotic divisions occur according to Polygonum-type development. After the first division of the megagametophyte, the nuclei migrate to opposite ends of the coenocytic megagametophyte, where they divide twice to form three antipodals at the chalazal end and the egg cell and two synergids at the micropylar end. The two remaining nuclei converge at the center of the cell to form polar nuclei. After all mitotic divisions are complete, cell walls are formed between the nuclei at both ends of the megagametophyte but not around the polar nuclei, resulting in an 8-nucleate, 7-celled megagametophyte which is wholly contained within the original spore wall. Ovules corresponding to each developmental timepoint were isolated and used for the comparative analysis of gene expression at the level of mRNA populations.

The present invention is based in part on the identification of genes which are expressed uniquely during ovule development as described above. These genes are of value because they play a role either in regulating development or in establishing the specialized identities of cells in the ovule. As explained in detail below, the genes of the invention were identified by differential screening of cDNA libraries. The isolated genes or their promoter sequences are then used in a variety of plant genetic engineering techniques to produce improved crop plants.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al, *Molecular Cloning—A Laboratory Manual,* 2nd. ed., Cold Spring Harbor Laboratory, Cold Spring Harbor, New York, (1989).

Isolation of nucleic acids of the invention

The isolation of sequences from the genes of the invention may be accomplished by a number of techniques. For instance, oligonucleotide probes based on the sequences disclosed here can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from ovules and a cDNA library which contains the gene transcript is prepared from the mRNA.

The cDNA or genomic library can then be screened using a probe based upon the sequence of a cloned ovule-specific gene such as the genes disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying ovule-specific genes from plant tissues are generated from comparisons of the sequences provided herein. For a general overview of PCR see *PCR Protocols: A Guide to Methods and Applications.* (Innis, M, Gelfand, D., Sninsky, J. and White, T., eds.), *Academic Press,* San Diego (1990).

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Use of nucleic acids of the invention to inhibit gene expression

The isolated sequences prepared as described herein, can be used in a number of techniques, for example, to suppress endogenous ovule-specific gene expression and thereby inhibit ovule formation. A particularly useful gene for this purpose is clone O39, which as described below, encodes a protein containing strong homology to the homeodomain DNA binding motif of transcription factors. The homolog identified in Arabidopsis, A20, can also be used. Thus, inhibition of expression of this gene is particularly useful in the inhibition of ovule development and production of seedless fruit in a variety of plant species.

Sequences from a gene, O40, encoding cytochrome P450 monooxygenase from pollen tubes, as desribed below, can be used to inhibit expression of these genes in pollen as well as other plant tissues. The cytochrome P450 monooxygenases constitute a large gene superfamily of membrane-bound enzymes which catalyze the oxidation of diverse and often overlapping substrates of both endogenous and xenobiotic origin in diverse organisms from bacteria to fungi, plants and animals.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA,* 85:8805–8809 (1988), and Hiatt et al., U.S. Pat. No. 4,801,340.

The nucleic acid segment to be introduced generally will be substantially identical to at least a portion of the endogenous ovule-specific gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of ovule-specific genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334:585–591 (1988).

Another method of suppression is sense suppression. Introduction of nucleic acid configured in the sense orientation has been recently shown to be an effective means by which to block the transcription of target genes. For an example of the use of this method to modulate expression of endogenous genes see, Napoli et al., *The Plant Cell* 2:279–289 (1990), and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Use of nucleic acids of the invention to enhance gene expression

Isolated sequences prepared as described herein can also be used to introduce expression of a particular ovule-specific or other gene or to enhance or increase endogenous gene expression. Where overexpression of a gene is desired, the desired gene from a different species may be used to decrease potential sense suppression effects.

In the case of cytochrome P450 monooxygenase genes, enhanced or introduced expression may be useful in increasing resistance to various plant pests and diseases as well as detoxification of herbicides. Enhanced or introduced expression of these genes may be useful in increasing biosynthesis of various compounds such as terpenoids, phenylpropanoids, gibberellins, fatty acids and sterols.

One of skill will recognize that the polypeptides encoded by the genes of the invention, like other proteins, have different domains which perform different functions. Thus, the gene sequences need not be full length, so long as the desired functional domain of the protein is expressed. Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

In other embodiments, the promoters derived from the ovule-specific genes of the invention can be used to drive expression of heterologous genes in an ovule-specific manner, such that desired gene products are present in the ovule, seed, or fruit. Suitable structural genes that could be used for this purpose include genes encoding proteins useful in increasing the nutritional value of seed or fruit. Examples include genes encoding enzymes involved in the biosynthesis of antioxidants such as vitamin A, vitamin C, vitamin E and melatonin. Other suitable genes encoding proteins involved in lipid, protein, and carbohydrate biosynthesis. Still other genes can be those encoding proteins involved in auxin and auxin analog biosynthesis for increasing fruit size, genes encoding pharmacetically useful compounds, and genes encoding plant resistance products to combat fungal or other infections of the seed.

Typically, desired promoters are identified by analyzing the 5' sequences of a genomic clone corresponding to the ovule-specific genes described here. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing et al., in *Genetic Engineering in Plants*, pp. 221–227 (Kosage, Meredith and Hollaender, eds. (1983)).

Preparation of recombinant vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumafaciens*, and other transcription initiation regions from various plant genes known to those of skill.

Alternatively, the plant promoter may direct expression of the ovule-specific gene in a specific tissue or may be otherwise under more precise environmental or developmental control. Such promoters are referred to here as "inducible" promoters. Examples of environmental conditions that may effect transcription by inducible promoters include anaerobic conditions, elevated temperature, or the presence of light.

Examples of promoters under developmental control include promoters that initiate transcription only in certain tissues, such as fruit, seeds, or flowers. As noted above, the promoters from the ovule-specific genes described here are particularly useful for directing gene expression so that a desired gene product is located in ovules or seeds.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulforon or Basta.

Production of transgenic plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

*Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts, pp.* 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera Asparagus, Atropa, Avena, Brassica, Citrus, Citrullus, Capsicum, Cucumis, Cucurbita, Daucus, Fragaria, Glycine, Gossypium, Helianthus, Heterocallis, Hordewn, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna, and, Zea.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

EXAMPLE

This example describes the isolation and characterization of exemplary ovule-specific genes.

METHODS

Plant Material

Individual orchid plants of the genus Phalaenopsis (cv. SM9108, Stewart Orchids) that were generated by mericloning, and thus genetically identical, were utilized for all material in this study. Plants were maintained under optimal growth conditions in the greenhouse at University of California, Davis. Flowers from these plants were randomly pollinated and ovaries harvested at appropriate times after pollination. After each harvest, tissues were immediately frozen in liquid nitrogen. A small sample of tissue from each timepoint was examined whole by light microscopy to confirm the stage of ovule development. Tissues harvested at 0, 1, and 4 weeks after pollination contain both ovary wall and meristematic ovule and placental tissues, which could not be separated due to the early stage of ovule development. Tissues harvested subsequently were separated into ovules and ovary wall by rapid dissection. The top and bottom of the ovaries were excised and discarded because the ovules at the extreme ends of the ovary were not generally at the same developmental stage, and then the remaining ~70% of the ovary was opened longitudinally with a sterile razor blade, effectively splitting it into sections representing the three locules. The thin layer of ovules along the placental region of each slice was dissected with a razor blade, taking care to avoid adjacent areas containing numerous hair cells (Zhang and O'Neill, *Plant Cell* 5:403–418 (1993)). Most pollen tubes were pulled out of the wall and ovule tissue prior to freezing, but by 5.5 weeks after pollination many pollen tubes were well intertwined with the ovules and could not be separated without damaging the tissue. The ovary wall tissue does, on the other hand, contain hair cells. Young leaves, roots and unpollinated flower parts were also removed with a sterile razor blade and immediately frozen in liquid nitrogen to represent vegetative and other reproductive organs of the plant.

Library Construction

Total RNA was isolated as described in O'Neill et al., *Plant Cell* 5:419–432 (1993). Poly(A)+ RNA was isolated using paramagnetic oligo(dT) beads (Dynabeads, Dynal) according to the manufacturer's suggestions. LiCl was removed from the poly(A)+ RNA by two ethanol precipitations prior to first strand cDNA synthesis. Libraries were constructed from 5 μg poly(A)+ RNA isolated from 5.5, 6.5, 7 and 11 WAP ovule tissue, as well as pollen tube tissue. RNA from 5.5 WAP ovule tissue was used for the archesporial cell-stage library, 11 WAP ovule tissue was used for the mature ovule library, and RNA from 6.5 and 7 WAP ovules was pooled for the construction of the megasporocyte-stage library. cDNA was constructed and cloned into the λZAPII phage vector (Stratagene) according to the manufacturer's protocol. The three ovule cDNA libraries each contain ~3×10⁶ clones, and the pollen tube cDNA library contains ~1.8×10⁶ clones, ≧95% of which contain inserts.

Library Screening

Three way differential screening was carried out with the 6.5/7 WAP and 11 WAP libraries. Approximately $2.0 \times 10^5$ clones from each library were plated out and three replica filters (Schleicher and Schuell BA85 nitrocellulose) were made from each plate. Each filter set was hybridized with first strand cDNA probes synthesized from either 6.5 or 11 WAP ovule poly(A)+ RNA as the experimental probes, or 6.5 combined with 11 WAP ovary wall poly(A)+ RNA as the control probe. cDNAs were labelled with $^{32}$P-dATP in 50 μl reverse transcription reactions containing 5 μg poly(A)+ RNA, 1.5 μg oligo(dT)12–18 (Pharmacia), 40 u. RNasin (Promega), 50 μM dATP, 500 μM dCTP, dGTP, and dTTP, 1× reverse transcriptase buffer (Gibco/BRL), 10 mM DTT, 12.5 μl [α-32P] dATP (6000 Ci/mmol) and 600 u. Superscript reverse transcriptase (Gibco/BRL) at 37° C. for one hour.

DNA and RNA Analysis

The methods employed for RNA extraction as well as RNA blot hybridization were as described in O'Neill et al., supra, except that 20 μg total RNA was used in each lane of the RNA gels. DNA was extracted from young leaves as described by Jofuku and Goldberg (Jofuku and Goldberg, 1988). 15 μg genomic DNA was digested with the restriction enzymes EcoRI, BamHI, or HindIII (Promega) according to standard procedures, reprecipitated by the addition of 0.3 M NaCl and 2.5 volumes 95% ethanol, resuspended in TE and electrophoresed on an 0.8% agarose gel for 12 hours at 4° C. The DNA was transferred to Nytran membranes (Schleicher and Schuell) by overnight capillary transfer according to standard procedures. Both RNA and DNA blots were hybridized with probes labelled to high specific activity by random priming (Prime-a-Gene kit, Promega) with 32P-dCTP as described in O'Neill et al., supra. RNA gel blots were hybridized at 42° C. for 48 hours in 50% formamide, 5× SSC, 0.05 M phosphate buffer (pH 6.5), 1× Denhardt's solution, 0.2 mg/ml sheared denatured salmon testes DNA (Sigma, Type III) and 0.2% SDS (Gibco/BRL) to which denatured labelled probe was added to a final concentration of 1.5×10⁶ cpm/ml hybridization solution. RNA blots were washed 1× at room temperature for 20 min. and 2× at 55° C. and 1× at 63° C. for 20 min. each wash in 0.2× SSC, 0.1% SDS, and 0.05 M phosphate buffer (pH 6.5). After stripping, all RNA blots were hybridized with a Phalaenopsis actin clone (Genbank accession number U18102) to confirm the presence of undegraded RNA in each lane. DNA gel blots were hybridized at 42° C. for 48 hours in 50% formamide, 5× SSC, 0.05 M phosphate buffer (pH 7.0), 5× Denhardt's solution, 0.2 mg/ml sheared denatured salmon testes DNA (Sigma, Type III) and 0.2% SDS (Gibco/BRL) to which denatured labelled probe was added to a final concentration of 5×10⁶ cpm/ml hybridization solution. DNA blots were washed 1× at room temperature for 20 min. and 2× at 55° C.

for 20 min. each wash in 0.2× SSC, 0.1% SDS, and 0.01% sodium pyrophosphate. Autoradiography was performed at −80° C. using Kodak XAR-5 film and one intensifying screen (Cronex Lightning Plus, DuPont). DNA blot hybridizations were exposed for 2–5 days, while each RNA blot hybridization experiment was exposed to film at least twice. The first exposure, which varied from 12 hours to 4 days, was calculated to be appropriate for photographic reproduction, while the final exposure was for 7 to 10 days in order to detect faint bands not apparent in shorter exposures.

Sequence Analysis

Clones were reconstituted as pBluescript plasmids from the λZAPII library by in vivo excision as described by the manufacturer's protocol (Stratagene). Sequencing was carried out by the dideoxynucleotide chain termination method (Sanger et al., *Proc. Natl. Acad. Sci.* 74:5463–5467 (1977)), using Sequenase v. 2 as suggested by the manufacturer (United States Biochemical/Amersham). Nested deletions were constructed by exodeletion using the Erase-a Base system (Promega) and by restriction digestion of the plasmids. In the case of some clones, sequence-specific primers were synthesized and used to generate overlapping sequence information. Sequence analysis and multiple sequence alignment (PILEUP) was accomplished using Genetics Computer Group (Madison, Wis.) and BLAST (Altschul et al., *J. Mol. Biol.* 215:403–410 (1990)) computer programs.

In Situ Hybridization

The fixation and embedding of tissues for in situ hybridization to mRNA in tissue sections was carried out as initially described for immunolocalization by Baskin et al., *Planta* 187:405–413 (1992) and subsequently described for detection of mRNA by Kronenberger et al., *Cell Biol. Int.* 17: 1013–1021 (1993), with a few modifications. Essentially, 1.0–1.5 mm slices of tissue were fixed in 4% paraformaldehyde (Sigma), 0.3% glutaraldehyde (Polysciences), 0.1% Triton X-100 (Sigma) in 0.05 M phosphate buffer (pH 7.0) for 1–4 hours at 4° C. Tissue was transferred to fresh fixative overnight, then rinsed three times with buffer alone to remove fixative. Tissue was dehydrated by passage through a graded ethanol series (10–100%) containing 1 mM DTT. The tissue was infiltrated with 4:1 (v/v) N-butyl-methacrylate: methyl-methacrylate (Ted Pella, Inc.) embedding material without DTT, which proved to be unnecessary and tended to make the resin brittle. The tissue was placed sequentially into 2:1, 1:1, then 1:2 EtOH:methacrylate mixture (v/v) for at least 12 hours at each step. Finally, tissue was placed into three changes of pure methacrylate solution for 24 hours each, which contained 0.5% bezoin ethyl ether and through which nitrogen gas had been bubbled to displace dissolved oxygen. Tissue was placed in plastic molds (Polysciences, #16643A) with fresh embedding media, covered with parafilm, and exposed to UV light supplied from 20 cm below the mold by a small hand-held long-wave UV source for 12–18 hours. All steps were carried out at 4° C. and all solutions and materials were made RNase free according to standard procedures (Sambrook et al., supra). Tissue was sectioned dry on glass knives with a Reichert-Jung ultramicrotome to 2.5 or 5 μm, then placed on drops of distilled water on Superfrost Plus microscope slides (Fisher). Sections were spread with chloroform and allowed to dry onto the slides overnight at 42° C.

Hybridization, washing and autoradiography was performed as described previously by our laboratory (Nadeau et al., *Plant Physiol.* 103:31–39 (1993)). Initially, the methacrylate embedding media was thoroughly removed by two washes in 100% acetone for 20 minutes each, with gentle stirring. Slides were then rinsed three times in water prior to BSA treatment. Proteinase K digestion was performed essentially as described, but 10 μg/ml Proteinase K (Boehringer-Mannheim Biochemicals) was employed rather 1 μg/ml. 35S-UTP labelled RNA probes were synthesized by in vitro transcription from pBluescript plasmids (Stratagene) using T7 and T3 RNA polymerases (Promega) as described previously. Probes were purified using DEPC-treated Chromaspin-100 columns (Clontech, Palo Alto, Calif.), and then sheared as previously described (Nadeau et al., supra). Hybridizations were carried out at 44° C. as previously described, except in the case of O39, in which case the hybridization was performed at both 44° C. and 50° C. Slides were air dried following the hybridization wash steps, and autoradiography was performed as previously described. Slides were exposed 7–21 days, as necessary. Slides were subsequently stained with 0.005% toluidine blue (w/v) in water, passed through an ethanol dehydration series to xylene, then mounted in Permount. An Olympus BX60 microscope was used for both lightfield, darkfield and fluorescence photography with Kodakcolor Gold or Ektar film (Kodak).

Microscopy

To visualize intact ovule structure, tissue was harvested directly into clearing solution composed of 1:1:1 chloroform: methyl salicylate:DMSO (v/v/v). After several hours at 4° C., tissue was mounted in the same media and photographed with differential interference contrast (Nomarski) microscopy using an Olympus BX50 microscope. Photographs were made with Kodak Gold 400 film.

RESULTS

Identification of cDNAs Expressed during Ovule Development

Three pivotal events in development of the female gametophyte were selected for analysis, based on their obvious significance to the development of a fertile ovule and because they represent events which seemed most likely to involve significant changes in gene expression. These stages are illustrated in FIG. 1. The first event targeted was the formation of the ovule primordia proper, as defined by finger-like meristematic projections and the cytological differentiation of the archesporial cell (early primordia library). Tissue corresponding to these stages was harvested 5.5 weeks after pollination (WAP). The second event targeted was the stage immediately before and during the transition to meiosis of the megasporocyte (megasporocyte library). Ovules at this stage of development have previously undergone integument initiation and further elongation of both inner and outer integuments is occurring through new cell divisions. The fully anatropous orientation of the ovules has been achieved by this stage of development. Ovule tissue representing these stages of development was harvested 6.5 weeks and 7.0 WAP, in order to include a range of late pre-meiotic and meiotic events. Finally, the late stages of ovule development including development and differentiation of the embryo sac were included in the final stage-specific ovule library (embryo sac library). This cDNA library was constructed with ovule tissue harvested 11 WAP and includes stages of development ranging from ovules undergoing the final mitotic divisions of embryo sac development to ovules with mature embryo sacs. This library should contain transcripts involved in such processes as polar redistribution of organelles within the embryo sac, differentiation of the cell types within the embryo sac and sporophytic tissues of the ovule, as well as transcripts involved in signaling between the female and male gametophytes.

The megasporocyte and embryo sac libraries were selected for the initial screening efforts. These libraries were subjected to three-way differential screening using cDNA probes reverse transcribed from ovary wall mRNA as control and ovule mRNA (6.5 and 11 WAP) as experimental probes. This strategy allowed identification of cDNA clones in each library that are characteristic of ovule tissue and to eliminate mRNAs shared with ovary tissue. It should be noted that screening in this way provided information about the abundance of mRNAs in the ovule relative to the ovary wall at both stages of development. Most genes related to photosynthesis and general housekeeping processes should be expressed in the ovary wall, and so clones selected by this strategy should represent genes which may not be unique to the ovule, but which are part of the contingent of genes that are responsible for the biochemical identity of cells in the ovule. This strategy also enabled initial observation of the stage-specificity of the clones identified as more abundant in ovule tissue.

160 clones were selected based on their greater abundance in ovule tissue as compared to ovary wall tissue at one or both stages examined, as well as 30 clones that were more abundant in ovary tissue. One quarter of the clones that were more abundant in ovule tissue were chosen for further analysis and carried through secondary and tertiary screens. Restriction digestion analysis and cross hybridization analysis of the resulting clones revealed a total of 8 unique sequence classes which were further analyzed.

Stage-specific Expression of Ovule cDNA Clones

To determine the pattern of expression of these genes during ovule development, and to confirm the differences in mRNA abundance observed in the screening process, each clone was used to probe RNA gel blots containing total RNA isolated from ovary or ovule tissue at various times after pollination. These timepoints correspond to stages of ovule development described in the timeline of Phalaenopsis ovule development (FIG. 1). Additionally, all RNA blots were probed with a Phalaenopsis actin clone to confirm the presence of undegraded RNA in each lane.

This analysis demonstrates that the two clones, O39 and O40, isolated from immature ovules 6.5 WAP are expressed at high steady-state levels at this developmental stage. O39 begins to be expressed at detectable levels at 5.5 WAP, and continues to be expressed up to the mature ovule stage at 11 WAP. Maximum transcript levels occur at 7 WAP. O40 also begins to be expressed at 5.5 WAP and is present at approximately the same abundance at 6.5 and 7.5 WAP, but is absent again by 11 WAP. At much longer autoradiographic exposure times (see Methods), O40 transcripts are faintly detectable at 4 and 11 WAP. The relative abundance of O40 transcripts is very high relative to that of O39, which required somewhat longer autoradiographic exposures. As can be seen from the timeline in FIG. 1, these clones are expressed at high levels during stages when several key events are occurring, including integument initiation and growth, morphological differentiation of the megasporocyte and subsequent entry into meiosis (5.5, 6.5 and 7.5 WAP).

Additionally, several clones (O108, O126, O141) isolated from nearly mature ovules also exhibit highly stage-specific patterns of expression. Transcripts corresponding to these clones are undetectable at early stages of development, even under long autoradiographic exposures, but are abundant at 11 WAP when ovules are completing embryo sac development and some fertilization events have occurred. A second class of clones (O129, O137) isolated from nearly mature ovules is detected in ovule tissue at all stages but increases in abundance reaching a maximum at 11 WAP. No ovule-specific clones isolated thus far were expressed before 5.5 WAP, a time when ovule primordia are forming.

Tissue-specific Expression of Ovule cDNA Clones

Each clone was used to probe RNA blots containing total RNA isolated from various organs of the Phalaenopsis plant to determine if the transcripts are present in other organs, or are restricted to ovule tissues. This analysis indicated that mRNAs corresponding to clones O39 and O40 are not found in the ovary wall, other floral organs such as the stigma or petals, or in other vegetative organs such as the leaves or roots. Clones O108 and O126 are specific to mature ovule tissues and are not detected in other tissues of the plant. Interestingly, O141 is present at high levels only in ovules but is also detectable at low levels in roots. The remaining clones (O129, O137) are present at quantitatively higher levels in ovule tissue, as would be expected from the screening strategy, but are present in all organs of the plant examined. It is probably significant that both clones (O129, O137), which were not stage specific in ovule tissues, are also expressed at some level in other tissues of the plant.

Sequences Homologous to Ovule cDNAs are Present in the Genome at Varying Abundance In order to determine the approximate number of sequences in the Phalaenopsis genome homologous to each cDNA clone, we hybridized each clone to genomic DNA digested with EcoRI, BamHI, and HindIII at moderately high stringency (see Methods). This analysis showed that O39, O40, O126 and O141 are present as single copy sequences. When the strongly hybridizing bands are considered, multiple fragments in each lane can be explained by restriction enzyme sites present in the cDNA. O40 shows fainter bands that may represent relate sequences. In the case of O108, O126 and O137 multiple bands of roughly equal intensity are present, indicating that these cDNAs are members of a small family of related sequences in the Phalaenopsis genome. In these cases, additional fainter bands are also apparent that may represent more divergent members of each gene family.

In Situ Hybridization Demonstrates that Some Ovule cDNAs are Cell-type Specific and Some are Expressed Throughout the Ovule In situ hybridization of all clones to tissue sections was carried out in order to precisely define the developmental stage of gene expression, a goal which can be most accurately addressed by actually observing the structural features of the ovules in which transcripts are found. Furthermore, we wanted to be able to define the specific cells of the ovule which express each ovule-specific clone identified. To attain the level of resolution necessary to identify specific cells within the ovule that express the gene of interest, we developed a technique that maintained the structural integrity of delicate tissues more completely than traditional paraffin embedding techniques. To do this, we embedded all tissues in a UV light-polymerized methacrylate plastic mixture. This approach is a modification of a procedure that has been used for immunolocalization studies (Baskin et al., supra) and has been described recently for in situ hybridization to RNA (Kronenberger et al., supra).

O39

Experiments carried out with O39 RNA probes to transverse sections through the orchid ovary at 3.5 WAP under high stringency conditions (see Methods) showed that very little, if any, O39 transcript is present in these tissues.

At the time of the archesporial cell differentiation in the ovule primordium, intense hybridization signal was apparent primarily in the primordia themselves rather than in the subtending placental regions. Interestingly, some hybridization was also apparent in the unique layer of placental epidermal cells that appear dense and secretory, and which are located on the side of the placenta where pollen tubes grow. No hybridization is observed in the parenchymatic epidermal cells that are located on the opposite side of the placenta.

Hybridization to transcripts in the ovule tissue is observable, although at a lower level, throughout subsequent ovule development. Very little hybridization is observed in the placental region of the ovary, with the exception of the placental epidermis.

In ovules undergoing the final mitotic divisions of megagametophyte development signal was observed in all cells of the ovule including the megagametophyte, though it was more clumped in appearance. This is a direct result of the increased vacuolization of the ovule cells at this stage, which has pushed the cell cytoplasm to the cell corners where signal is now localized. Once again, it was clear the layer of secretory cells on the outside of the placenta also show hybridization to the O39 probe though these tissues are not illustrated in this panel.

These observations agree well with those obtained by RNA blot hybridization analysis, which shows almost undetectable levels of O39 transcript in ovule tissue until 5.5 WAP, when transcript is clearly detected. O39 continues to be expressed throughout ovule development and is still present at 11 WAP, when ovules are mature.

O40

In situ hybridization of clone O40 to transverse sections of the orchid ovary demonstrated that, contrary to RNA blot hybridization results, clone O40 is expressed exclusively in the pollen tubes. The identification of this gene by the differential screening strategy is not completely unexpected, as pollen tubes become intertwined with the ovules in the ovary and consequently contribute to the RNA population harvested despite our attempts to remove them (see Methods).

O40 transcript is present at very low levels observable in long autoradiographic exposures at 4 WAP, and at high levels beginning at 5.5 WAP, as are transcripts from clone O39. O40 continues to be expressed at 6.5 and 7 WAP, throughout the process of meiosis and integument growth of the ovule. In contrast to O39, however, the abundance of O40 transcript levels are dramatically reduced at 11 WAP. The low level of O40 transcript in tissue at 4 WAP probably reflects the method of tissue collection at this timepoint. At 4 WAP there is little representation from the pollen tubes in the RNA because the whole population of pollen tubes has not penetrated to the middle of the ovary, and the pollen tube tips are not intertwined with the ovules at this stage of development. Tissue harvested at 11 WAP, on the other hand, definitely contains pollen tubes, so the low levels of O40 expression at 11 WAP in RNA blot hybridization analysis cannot be explained by the limitations in tissue collection.

O108

In situ hybridization of clone O108 to transverse sections through the orchid ovary when ovules are immature showed no hybridization to tissues of the ovule, placenta or pollen tubes prior to maturation of the ovule. There was, however, a large amount of hybridization to mature ovules, a finding consistent with RNA blot hybridization analysis that shows expression of O108 only at 11 WAP. Moreover, when ovules were observed to express O108 transcripts, signal is present only in the outer layer of the outer integument and in the megagametophyte. Because each section of ovary contains 20–50 ovules that are more-or-less randomly oriented, observation of numerous ovules in many different planes of section was possible. It was clear from observation of many different sections that, within ovules which show hybridization signal, the relative abundance of transcript is approximately the same throughout the layer of cells expressing the gene.

The results showed that all ovules in a given area of the ovary do not express the gene at equivalent levels, and interestingly, many ovules do not express the gene at detectable levels. Ovules which do not express O108 are interspersed randomly with those that do, such that examination of numerous sections did not reveal a discernible spatial pattern which might explain this observation. This pattern of expression within the ovule population as a whole indicates that expression of O108 most likely occurs within a narrow developmental window, such that small differences in stage between neighboring ovules results in the presence or absence of O108 transcripts. O108 is not present in other tissues of the ovary such as the hair cells which are derived from the inner ovary wall, or the pollen tubes. Additionally, background levels of hybridization to the placenta were observed, reinforcing data from RNA blot hybridization analysis that suggests O108 gene expression is strictly ovule-specific.

In situ hybridization to fertilized ovules, which are readily recognizable due to the subsequent rapid elongation of the outer integument, suggests that O108 continues to be expressed in the outer integument and embryo sac. The spatial pattern of cells which express the gene remains the same, however, although hybridization signal intensity is reduced and completely absent in some ovules at this stage. This suggests that the domain of expression of O108 does not shift during development, and that expression of O108 is turned off or down-regulated following fertilization.

O141

In situ hybridization of immature ovules to clone O141 RNA probes shows no hybridization signal, indicating that expression of this gene is also very stage specific as has been observed at the level of RNA blot hybridization. Hybridization to mature or nearly mature ovules was present in both cell layers of the outer integument of the mature ovule, rather than only the outermost layer of the outer integument as was observed with clone O108. No other tissues of the ovule were ever observed to show hybridization to O141 above background levels even in very long exposures of several months. Similar to the pattern observed for O108, O141 hybridizes to only a subset of ovules in each section observed. This indicates that O141 is expressed only in a narrow window of time, such that the slight differences in developmental stage of neighboring ovules is reflected in O141 gene expression. In the case of O141, however, gene expression most likely begins after fertilization. All the ovules in which the gene is expressed show the elongated outer integument characteristic of post-fertilization ovules. Furthermore, most ovules that express O141 mRNA have integuments that appear slightly degraded in appearance. This characteristic is not a procedural artifact, but accurately represents the condition of the ovules as they rapidly progress towards seed maturity following fertilization.

Sequence Analysis Suggests that the Ovule cDNAs Function at Different Levels of Gene Regulatory Hierarchies Clone O39 Encodes a Homeobox Transcription Factor Clone O39 represents an apparently full-length mRNA of 3088 nt containing one long open reading frame (ORF) from position 298 to 2593 (SEQ ID No: 1). This ORF encodes a protein of 798 amino acids with a calculated molecular weight of approximately 84 kD and pI of 5.98 (SEQ ID No: 2). Sequence analysis indicated that a region located near the amino-terminal end of the protein exhibits strong homology to the homeodomain DNA binding motif of transcription factors. The archetypal homeodomain consists of approximately 61 amino acids which form a helix-turn-helix structure capable of sequence-specific DNA binding (Scott et al., Biochim. Biophys. Acta 989:25–48 (1989)). The predicted sequence of O39 retains all four of the absolutely conserved amino acids in the third recognition helix of the homeodomain as well as 9 of the 17 most highly conserved amino acids present throughout the homeodomain and thus encodes a true homeobox transcription factor. As is the case between other homeobox protein families, O39 exhibits little sequence similarity to other homeobox protein families outside the homeobox region (Duboule, *Guidebook to the Homeobox Genes*, Oxford University Press (1994)). A notable exception is the recently identified GLABRA2 homeodomain protein which regulates trichome differentiation in Arabidopsis (Rerie et al., *Genes Dev.* 8:1388–1399 (1994)). Amino acid sequence identity between O39 and GLABRA2 is 39% over the entire length of the protein and 66% within the homeodomain region; overall structural organization is also similar between the two proteins, with the homeobox in the amino-terminal end of the protein. Additionally, O39 encodes a larger protein than most homeobox proteins, as does the GLABRA2 gene (798 compared to 660 amino acids). When compared to other plant homeodomain proteins, the O39 homeodomain is most similar to Athb-1 and -2 (HAT4 and HAT5) from Arabidopsis (Ruberti et al., *EMBO J.* 10:1787–1791 (1991); Schena and Davis, *Proc. Natl. Acad. Sci. USA* 89:3894–3898 (1992) and least similar to the maize protein KNOTTED1 (Vollbrecht et al., *Nature* 350:241–243 (1991).

The cDNA also contains four short ORFs in the 5' untranslated region (UTR) of the transcript that are followed by stop codons. The final three ORFs, which contain 6, 19 and 6 codons respectively, are in frame with the final and presumed coding region of the transcript. Although this structural feature has no known function in plants, short ORFs in the 5' UTR of the yeast GCN4 mRNA are involved in the translational control of expression of this transcription factor (Hinnebusch, *Trends. Bioch. Sci.* 15:148–152 (1990)), and short ORFs have been observed in the 5' UTR of several plant homeobox genes (Ruberti et al., supra; Bellmann and Werr, *EMBO J.* 11:3367–3374 (1992); Schindler et al., *Plant J.* 4:137–150 (1993)) and in the transcripts of several other types of gene regulatory proteins in plants (Hartings et al., *EMBO J.* 8:2795–2801 (1989); Singh et al., *Plant Cell* 2:891–903 (1990)).

Using standard hybridization techniques using a cDNA library prepared from Arabidopsis buds, a homologous gene, A20, was identified (SEQ ID NO: 11 and SEQ ID NO: 12).

Clone O40 Encodes a Cytochrome P450 Mixed Function Monooxygenase

Sequence analysis of clone O40 indicates that the largest ORF encodes a cytochrome P450 monooxygenase of predicted molecular weight 48 kD and a pI of 6.62 (SEQ ID NO: 3 and SEQ ID NO: 4). These enzymes are known to catalyze a wide variety of oxidative reactions in animals, including the metabolism of steroids, biogenic amines, fatty acids, prostaglandins and leukotrienes, as well as the detoxification of xenobiotic substances.

In plants, cytochrome P450 monooxygenases are known to play a role in the biosynthesis of terpenoids, phenylpropanoids, gibberellins, fatty acids and sterols, as well as the detoxification of herbicides (Donaldson and Luster, *Plant Physiol* 96: 669–674 (1991)). These enzymes are membrane bound and employ a heme group linked to the polypeptide through a cysteine residue in the motif FxxGxxxCxxG (SEQ ID No: 13), (where x is a non-conserved amino acid) which is present in all cytochrome P450s. Catalytic activity is accomplished by complexing of the substrate with the heme moiety, which then acts to transfer an electron from the donor NADPH-reductase to molecular oxygen, resulting in the reduction of molecular oxygen to H2O and the oxidation of the substrate.

The O40 gene product may play a role in the biosynthesis of a hormone involved in intercellular communication. In animals, cytochrome P450s are known to catalyze multiple steps in the metabolism of steroid hormones such as testosterone and estrogen. Related substances such as androgen and estrogen have been tentatively identified in several plant species (Simons and Grinwich, *Can. J. Bot.* 67:288–296 (1989)) and have been suggested to play a role in aspects of reproduction such as sex expression and floral induction, (see, e.g., Zhang et al., *Sex. Plant Reprod.* 4:193–196 (1991)).

O40 might also play a role in the biosynthesis of non-polar plant growth substances, such as the recently cloned Dwarf3 locus (Winkler and Helentaris, *Plant Cell* 7:1307–1317 (1995)). This gene encodes a cytochrome P450 belonging to a new family (CYP88) which is thought to catalyze one of the early steps in the biosynthesis of gibberellin. Recent study of the gibberellin mutant gib-1 in tomato has shown that GA deficiency causes arrest of the pollen mother cells in G1 phase of pre-meiotic interphase, which is reversible by exogenous application of GA (Jacobsen and Olszewsi, *Plant Physiol.* 97:409–414 (1991), suggesting that it is possible that GAs play a role in the further development of the pollen tube.

Alternatively, O40 may play a role in the biosynthesis of plant hormones such as abscisic acid or brassinosteroids. Pollen has long been known to be a rich source of brassinosteroid compound (Mandava, *Ann. Rev. Plant Physiol.* 39:23–52 (1988)). It is known that brassinosteroids can induce elongation or swelling of tissues as well as induce cell division when applied to various plant tissues.

Finally, the O40 gene product can be involved in the biosynthesis of a secondary metabolite found in the pollen tube. Work with chalcone synthase (CHS) deficient plants has shown that pollen germination requires the presence of specific flavonols, and that male fertility of CHS-deficient plants can be restored by application of these flavonols to the stigma (Mo et al., *Proc. Natl. Acad. Sci. USA* 89:7213–7217 (1992)). This work clearly shows that secondary metabolites can play a crucial role in developmental events, in this case pollen hydration and growth.

The complexity of evolutionary relationships between the families of cytochrome P450s has lead to the arbitrary convention that sequences exhibiting ≦40% identity are considered to be members of different gene families (Nebert and Gonzalez, *Ann. Rev. Biochem.* 56: 945–993.1987). By the same token, sequences within a family are to be considered members of the same gene subfamily if they share ≧68% similarity. O40 is the first orchid cytochrome P450 identified, and by this convention, it represents the second member of the CYP78 gene family and has consequently been named CYP78A2 by the Cytochrome P450 Gene Nomenclature Committee.

The amino acid sequence of O40 is most similar to MTC1 (CYP78A1) from *Zea mays*, with which it shows 54% amino acid identity. O40 also shares sequence homology with several other recently identified plant cytochrome P450s, including 35% amino acid identity with CYP71A1 from *Persea americana,* which increases in abundance in the pericarp during ripening. When compared to a number of other plant cytochrome P450s, O40 exhibits 35% identity with flavonoid-3', 5'-hydroxylase from *Petunia hybrida* and 29% identity with cinnamate 4-hydroxylase from *Helianthus tuberosus* and *Phaseolus aureus,* respectively.

Clone O108 Encodes a Novel Peptide of Unknown Function

Clone O108 contains several ORFs, the longest one which codes for a putative protein product of approximately 15 kD and has a predicted pI of 5.37 (SEQ ID NO: 5 and SEQ ID NO: 6). Comparison of the sequence of this clone to the database of known sequences revealed no obvious homology to genes of known function, but showed significant homology to an expressed sequence tag (EST) from Arabidopsis. The putative protein encoded by O108 contains a consensus ATP/GTP binding site at the C-terminal end, a characteristic shared by the predicted peptide encoded by the EST clone.

Clone O126 Encodes a Glycine-rich Protein

Clone O126 is 867 bp in length (SEQ ID No: 7). The most reasonable ORF encodes an approximately 18 kD protein rich in glycine residues, with a predicted pI of 3.71 (SEQ ID No: 8). The putative protein contains a probable signal peptide sequence, minus several residues of the signal peptide and the initial methionine, making it likely that the protein is secreted to the cell wall. Overall, the putative protein is 31% glycine, and 42% glycine within the glycine-rich region from residue 45 to 190. This falls well within the range for glycine-rich proteins that are thought to be structural components of the plant cell wall. Moreover, as in other cell wall glycine-rich proteins, O126 contains a slightly irregular repeated sequence motif that is found four times with a fifth partial repeat. The protein does not, on the other hand, contain the consensus ribonucleotide binding domain found in several plant glycine-rich proteins that appear to be localized to the cytoplasm, nor does it show homology to heterogeneous nuclear ribonuclear protein A1. These characteristics lead us to believe that O126 is a cell wall structural protein similar to those isolated from a variety of monocot and dicot species. Significant sequence homology in the higher order repeats or in the residues interspersed with glycine residues has not been observed between O126 and other reported sequences, however, suggesting that O126 is a novel glycine-rich protein which we have named PGRP-1. In fact, the glycine-rich domain of the protein is highly acidic, containing 10% aspartate and 3.5% glutamate, in contrast to the majority of reported glycine-rich proteins which are either hydrophobic or basic in nature.

Clone O141 is Homologous to Cysteine Proteinases

Sequence analysis of clone O141 reveals that the 1347 bp cDNA encodes a putative protein of approximately 40 kD and predicted pI of 6.36 (SEQ ID NO: 9 and SEQ ID NO: 10). The length of the cDNA is slightly shorter than the 1.4 kb mRNA observed by RNA gel blot hybridization, such that the ORF most likely begins at position 12 of the cDNA. The predicted polypeptide is most similar to endopeptidases from *Vigna mungo, Phaseolus vulgans, Vicia sativa* and *Glycine max,* with which it shares 67, 66, 64 and 60% overall identity, respectively (Mitsuhashi and Minamikawa, *Plant Physiol.* 89:274–279 (1989); Kalinski et al., *J. Biol. Chem.* 265:13843–13848 (1990); Tanaka et al., *Plant Mol. Biol.* 16:1083–1084 (1991)). The predicted polypeptide also shares significant identity with the well characterized fruit endopeptidases papain (43%) and actinidin (45%), as well as the aleurone specific endopeptidase aleurain (39%) (Rogers et al., *Proc. Natl. Acad. Sci. USA* 82:6512–6516 (1985); Cohen et al., *Gene* 48:219–227 (1986); Praekelt et al., *Plant Mol. Biol.* 10:193–202 (1988)). It is likely that O141 encodes an authentic endopeptidase activity, since it contains the consensus sequences surrounding the three key amino acids critical to catalysis (Cys155, His290, Asn311 of O141) and contains 10 of 14 type II glycine residues which are important to the overall protein conformation (Kamphuis et al., *J. Mol. Biol.* 182:317–329 (1985).

Examination of the predicted amino acid sequence suggests that the first 19 residues represent a signal sequence which is cotranslationally removed from the protein to yield a 38 kD product. Alignment of the O141 sequence with the mature peptides of other cysteine proteinases suggests that it also may be processed to produce a mature 25 kD protein in a manner similar to other cysteine proteinases, most likely by proteolytic cleavage before the leucine in position 131. There is evidence that removal of the prosequences of both papain and the *V. mungo* cotyledon enzyme results in activation of the enzyme. The similarity between O141 and these proteins suggests that it also may undergo conversion to an active peptide, thus possibly providing a mechanism to limit enzyme activity to the appropriate cellular compartment or developmental milieu. Interestingly, both O141 and the cysteine proteinases to which it is most similar contain endoplasmic reticulum retention signals at the C-terminal end (Denecke et al., *EMBO J.* 11:2345–2355 (1992)), suggesting that they might normally function in this cellular compartment. O141 does not contain potential glycosylation sites in the mature or prosequences of the peptide, unlike several similar proteinases which are thought to be transported through the secretory pathway.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. An isolated nucleic acid construct comprising a polynucleotide sequence from an ovule-specific gene, wherein the polynucleotide sequence hybridizes to O39 (SEQ ID No: 1), O108 (SEQ ID No: 5), O126 (SEQ ID No: 7), O141 (SEQ ID No: 9), or A20 (SEQ ID No: 11) under stringent conditions.

2. The nucleic acid construct of claim 1, wherein the polynucleotide sequence hybridizes under stringent conditions to SEQ ID NO: 1 and encodes, a protein of about 84 kD.

3. The nucleic acid construct of claim 2, wherein the polynucleotide sequence is O39 (SEQ ID No: 1).

4. The nucleic acid construct of claim 1, wherein the polynucleotide sequence hybridizes under stringent conditions to SEQ ID NO: 5 and encodes a protein of about 48 kD.

5. The nucleic acid construct of claim 4, wherein the polynucleotide sequence is O108 (SEQ ID No: 5).

6. The nucleic acid construct of claim 1, wherein the polynucleotide sequence hybridizes under stringent conditions to SEQ ID NO: 7 and encodes a protein of about 15 kD.

7. The nucleic acid construct of claim 6, wherein the polynucleotide sequence is O126 (SEQ ID No: 7).

8. The nucleic acid construct of claim 1, wherein the polynucleotide sequence hybridizes under stringent conditions to SEQ ID NO: 9 and encodes a protein of about 18 kD.

9. The DNA construct of claim 8, wherein the polynucleotide sequence is O141 (SEQ ID No: 9).

10. The DNA construct of claim 1, wherein the polynucleotide sequence is A20 (SEQ ID No: 11).

11. The nucleic acid construct of claim 1, further comprising a promoter operably linked to the polynucleotide sequence.

12. The nucleic acid construct of claim 11, wherein the polynucleotide sequence is linked to the promoter in an antisense orientation.

13. The nucleic acid construct of claim 11, wherein the promoter is an ovule-specific promoter.

14. An isolated nucleic acid construct which encodes a polypeptide having the amino acid sequence shown in SEQ ID No: 2, SEQ ID No: 6, SEQ ID No: 8, SEQ ID No: 10, or SEQ ID No: 12).

15. A transgenic plant comprising a recombinant expression cassette comprising a plant promoter operably linked to a polynucleotide sequence which hybridizes to O390 (SEQ ID No: 1), O108 (SEQ ID No: 5), O126 (SEQ ID No: 7), O141 (SEQ ID No: 9), or A20 (SEQ ID No: 11) under stringent conditions.

16. The transgenic plant of claim 15, wherein the plant promoter is a heterologous promoter.

17. The transgenic plant of claim 15, wherein the polynucleotide sequence is linked to the promoter in an antisense orientation.

18. The transgenic plant of claim 15, wherein the polynucleotide sequence is O39 (SEQ ID No: 1).

19. An isolated nucleic acid construct comprising a polynucleotide sequence which hybridizes to O40 (SEQ ID No: 3) under stringent conditions.

20. The nucleic acid construct of claim 19, wherein the nucleic acid encodes a protein of about 48 kD.

21. The nucleic acid construct of claim 19, wherein the polynucleotide sequence is O40 (SEQ ID No: 3).

22. An isolated nucleic acid construct comprising a polynucleotide sequence which encodes a polypeptide having the amino acid sequence as shown in SEQ ID No: 4.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 3060 base pairs
      (B) TYPE: nucleic acid
      (C) STRANDEDNESS: single (D) TOPOLOGY: linear (ii) MOLECULE TYPE: DNA (genomic)

(ix) FEATURE:
              (A) NAME/KEY: CDS
              (B) LOCATION: 291..2597
              (D) OTHER INFORMATION: /note= "clone O39 ovule-specific gene
                  from Phalaenopsis"

(xi) SEQUENCE DESCRIPTION: SEQ ID NO:1:

```
CTTGTTCCTC ACCCTTTCCT CTTCCCTTTC CCTGCAACCC TTTTCAGCTT CCATGGCATC      60

CTCTTTTTCT CTGTATCGAC TTCATCTTCT CTCACCTCTG CATGCACTCA CGTAGATCTT     120

AGCTCTTCTA TCCATTCCTC CTTATTTTTC TCAGCTTTCT GGTGATATAT TGTTCTTTTA     180

ACTTTTCTTC TCTCTAACTG AGCTCTGAAG AAATGGAGAA ACCAAAGAAA GGTTGCAGTG     240

AACGGAATCC CATGAGTGGG AGAAGAAATT AGGGTTTGTT GGAGCAAAAT ATG CTT        296
                                                        Met Leu
                                                          1

GCC GGC GTC ATG ATT CCG GCA AGA CAG GTA CCT TCG ATG ATC GGC AGG       344
Ala Gly Val Met Ile Pro Ala Arg Gln Val Pro Ser Met Ile Gly Arg
         5                  10                 15

AAC TCT TCA GCG TTG ACC TTA GCT CAG ATC AAT ATC TTG GAA GGC CAA       392
Asn Ser Ser Ala Leu Thr Leu Ala Gln Ile Asn Ile Leu Glu Gly Gln
         20                 25                 30

CAA CTC CCT CTT CAG CAC CAA CTC GCC GAA CTG ACG GCA CAA GCG ACG       440
Gln Leu Pro Leu Gln His Gln Leu Ala Glu Leu Thr Ala Gln Ala Thr
 35                 40                 45                 50

ACG ACG GCG GAG AGT GAC ATG ATG AGG GCT CGA GAA GAC GAC TTC GAG       488
Thr Thr Ala Glu Ser Asp Met Met Arg Ala Arg Glu Asp Asp Phe Glu
                 55                 60                 65

AGC AAG TCC GGC AGC GAT AAC ATC GAG GGC GGC TCC GGC GAT GAA CAC       536
Ser Lys Ser Gly Ser Asp Asn Ile Glu Gly Gly Ser Gly Asp Glu His
             70                 75                 80

GAT CCC AAT CAG CGA CCG AGG AAG AAG AGA TAC CAC AGG CAC ACT CAG       584
Asp Pro Asn Gln Arg Pro Arg Lys Lys Arg Tyr His Arg His Thr Gln
         85                 90                 95

CAC CAA ATT CAG GAA ATG GAA GCT TTT TTT AAG GAA TGC CCG CAT CCG       632
His Gln Ile Gln Glu Met Glu Ala Phe Phe Lys Glu Cys Pro His Pro
    100                105                110

GAT GAC AAG CAG AGA AAG GCG CTC AGT AAG GAG CTG GGA TTG GAA CCA       680
Asp Asp Lys Gln Arg Lys Ala Leu Ser Lys Glu Leu Gly Leu Glu Pro
115                120                125                130

CTA CAA GTG AAG TTT TGG TTT CAG AAC AAG CGC ACG CAA ATG AAG ACA       728
Leu Gln Val Lys Phe Trp Phe Gln Asn Lys Arg Thr Gln Met Lys Thr
                135                140                145

CAG CAT GAC AGA CAA GAG AAT TCA CAG CTT AGG GCA GAG AAC GAT AAG       776
Gln His Asp Arg Gln Glu Asn Ser Gln Leu Arg Ala Glu Asn Asp Lys
            150                155                160

CTG CGG AAT GAA AAC CTG CGG TAT AAG GAA GCA CTG AGC AAT GCC TCA       824
Leu Arg Asn Glu Asn Leu Arg Tyr Lys Glu Ala Leu Ser Asn Ala Ser
        165                170                175

TGC CCT AAC TGC GGC GGC CCA GCT ACA CTT GGG GAG ATG TCG TTT GAC       872
Cys Pro Asn Cys Gly Gly Pro Ala Thr Leu Gly Glu Met Ser Phe Asp
    180                185                190

GAG CAC CAC CTC AGG ATT GAG AAC GCC AGG CTG AGA GAA GAG ATA GAC       920
Glu His His Leu Arg Ile Glu Asn Ala Arg Leu Arg Glu Glu Ile Asp
195                200                205                210

AGG ATC TCC GGC ATT GCT GCA AAA TAC GTA GGC AAG CCA ATG AAC TCA       968
Arg Ile Ser Gly Ile Ala Ala Lys Tyr Val Gly Lys Pro Met Asn Ser
                215                220                225
```

```
TAC CCT CTC CTC TCC CCC ACT CTC CCA TCC CGC TCA TCA CTG GAC CTC        1016
Tyr Pro Leu Leu Ser Pro Thr Leu Pro Ser Arg Ser Ser Leu Asp Leu
            230                 235                 240

GGC GTC GGC GGA TTC GGC CTT CAC TCT CCC ACA ATG GGC GGC GAC ATG        1064
Gly Val Gly Gly Phe Gly Leu His Ser Pro Thr Met Gly Gly Asp Met
        245                 250                 255

TTT TCC CCA GCC GAG CTA CTG CGG TCC GTC GCC GGC CAA CCG GAG GTC        1112
Phe Ser Pro Ala Glu Leu Leu Arg Ser Val Ala Gly Gln Pro Glu Val
260                 265                 270

GAC AAG CCA ATG GTT ATC GAA CTG GCG GTT GCA GCC ATG GAA GAG CTG        1160
Asp Lys Pro Met Val Ile Glu Leu Ala Val Ala Ala Met Glu Glu Leu
275                 280                 285                 290

ATC AGG ATG GCT CAG CTG GGG GAA CCG CTG TGG ACT AGC AGT CCT GGT        1208
Ile Arg Met Ala Gln Leu Gly Glu Pro Leu Trp Thr Ser Ser Pro Gly
                295                 300                 305

TTG GAT GGA GGT AAT GAG ATT CTG AAT GAA GAG GAG TAT GTG CAG AAT        1256
Leu Asp Gly Gly Asn Glu Ile Leu Asn Glu Glu Glu Tyr Val Gln Asn
            310                 315                 320

TTT CCG AGA GGG ATT GGG CCG AAG CCG TTT GGA TTG AAG TCG GAG GCG        1304
Phe Pro Arg Gly Ile Gly Pro Lys Pro Phe Gly Leu Lys Ser Glu Ala
        325                 330                 335

TCG AGG GAG ACG GCC GTG GTG ATC ATG AGT CAT GTT AAT TTG GTT GAG        1352
Ser Arg Glu Thr Ala Val Val Ile Met Ser His Val Asn Leu Val Glu
340                 345                 350

ATT CTC ATG GAT GCG AAT CAA TGG TCG ACA ATG TTC TCC GGC ATT GTA        1400
Ile Leu Met Asp Ala Asn Gln Trp Ser Thr Met Phe Ser Gly Ile Val
355                 360                 365                 370

TCG AGG GGT ATG ACT CTT GAG GTA CTA TCA ACT GGT GTG GCT GGA AAC        1448
Ser Arg Gly Met Thr Leu Glu Val Leu Ser Thr Gly Val Ala Gly Asn
                375                 380                 385

TAC AAT GGT GCA CTG CAA GTG ATG ACA GCT GAA TTC CAA GTT CCA TCT        1496
Tyr Asn Gly Ala Leu Gln Val Met Thr Ala Glu Phe Gln Val Pro Ser
            390                 395                 400

CCT CTC GTT CCA ACT CGC GAA AGC TAC TTC GTT AGA TAC TGC AAA CAA        1544
Pro Leu Val Pro Thr Arg Glu Ser Tyr Phe Val Arg Tyr Cys Lys Gln
        405                 410                 415

CAT CCG GAC GGA ACT TGG GCG GTC GTC GAC GTC TCC TTG GAC AGT CTT        1592
His Pro Asp Gly Thr Trp Ala Val Val Asp Val Ser Leu Asp Ser Leu
420                 425                 430

CGC CCG AGC AGT CTT ATG ATG AGA TGC CGA AGA AGG CCT TCA GGA TGT        1640
Arg Pro Ser Ser Leu Met Met Arg Cys Arg Arg Arg Pro Ser Gly Cys
435                 440                 445                 450

TTG ATA CAA GAA ATG CCA AAT GGC TAC TCT AAG GTG ATT TGG GTA GAA        1688
Leu Ile Gln Glu Met Pro Asn Gly Tyr Ser Lys Val Ile Trp Val Glu
                455                 460                 465

CAT TTT GAA GTT GAT GAT AGG TCT GTT CAT AGT ATC TAC AAG CCA TTG        1736
His Phe Glu Val Asp Asp Arg Ser Val His Ser Ile Tyr Lys Pro Leu
            470                 475                 480

GTG AAC TCT GGC ATT GCA TTT GGG GCC AAA AGG TGG GTT TCT ACT TTG        1784
Val Asn Ser Gly Ile Ala Phe Gly Ala Lys Arg Trp Val Ser Thr Leu
        485                 490                 495

GAT CGA CAG TGC GAA CGC CTT GCA AGT GTC ATG GCT AGT AGC ATT CCA        1832
Asp Arg Gln Cys Glu Arg Leu Ala Ser Val Met Ala Ser Ser Ile Pro
500                 505                 510

TCG GGA GAA ATT GGA GTG ATA ACA ACA TCG GAG GGG AGA AAG AGC ATG        1880
Ser Gly Glu Ile Gly Val Ile Thr Thr Ser Glu Gly Arg Lys Ser Met
515                 520                 525                 530

CTG AAG CTA GCA GAG AGA ATG GTG CTT AGC TTT TGT GGA GGG GTG AGT        1928
Leu Lys Leu Ala Glu Arg Met Val Leu Ser Phe Cys Gly Gly Val Ser
                535                 540                 545
```

```
GCT TCA ACC ACT CAT CAA TGG ACG ACG TTA TCT GGA AGC GGC GCT GAA    1976
Ala Ser Thr Thr His Gln Trp Thr Thr Leu Ser Gly Ser Gly Ala Glu
            550                 555                 560

GAT GTG AGG GTG ATG ACC AGA AAA AGT GTA GAC GAT CCG GGC AGG CCC    2024
Asp Val Arg Val Met Thr Arg Lys Ser Val Asp Asp Pro Gly Arg Pro
            565                 570                 575

CCT GGT ATT GTT CTG AAT GCT GCA ACT TCA TTC TGG CTT CCT GTG TCT    2072
Pro Gly Ile Val Leu Asn Ala Ala Thr Ser Phe Trp Leu Pro Val Ser
            580                 585                 590

CCA AAA AGG GTT TTT GAT TTC CTC CGT GAT GAG AGT TCT CGT AGC GAG    2120
Pro Lys Arg Val Phe Asp Phe Leu Arg Asp Glu Ser Ser Arg Ser Glu
595                 600                 605                 610

TGG GAT ATC CTC TCG AAC GGC GGA GTA GTT CAG GAA ATG GCT CAT ATC    2168
Trp Asp Ile Leu Ser Asn Gly Gly Val Val Gln Glu Met Ala His Ile
            615                 620                 625

GCC AAT GGT CGA GAT CAT GGC AAC TGT GTT TCT CTT CTC CGT GTC AAT    2216
Ala Asn Gly Arg Asp His Gly Asn Cys Val Ser Leu Leu Arg Val Asn
            630                 635                 640

AGC ACA AAT TCA AAC CAA AGC AAC ATG CTG ATA CTC CAA GAG AGC TGC    2264
Ser Thr Asn Ser Asn Gln Ser Asn Met Leu Ile Leu Gln Glu Ser Cys
            645                 650                 655

ACT GAT CCC ACA GGC TCT TAT GTG ATA TAT GCT CCT GTG GAT GTG GTT    2312
Thr Asp Pro Thr Gly Ser Tyr Val Ile Tyr Ala Pro Val Asp Val Val
660                 665                 670

GCC ATG AAT GTG GTT CTC AAT GGA GGA GAT CCC GAC TAT GTG GCT CTC    2360
Ala Met Asn Val Val Leu Asn Gly Gly Asp Pro Asp Tyr Val Ala Leu
675                 680                 685                 690

TTG CCT TCA GGT TTC GCC ATC CTT CCT GAT GGC TCG AAT GGG GTT CAT    2408
Leu Pro Ser Gly Phe Ala Ile Leu Pro Asp Gly Ser Asn Gly Val His
                695                 700                 705

GGT GGT GGA AGT GGA ATC GGT GAG GTT GGA TCT GGT GGT GGT TCT CTG    2456
Gly Gly Gly Ser Gly Ile Gly Glu Val Gly Ser Gly Gly Gly Ser Leu
            710                 715                 720

CTT ACA GTT GCA TTC CAG ATA TTG GTT GAT TCA ATA CCA ACA GCA AAG    2504
Leu Thr Val Ala Phe Gln Ile Leu Val Asp Ser Ile Pro Thr Ala Lys
            725                 730                 735

CTG TCA CTT GGT TCT GTT GCG ACG GTT AAC AGC CTA ATT GCT TGC ACT    2552
Leu Ser Leu Gly Ser Val Ala Thr Val Asn Ser Leu Ile Ala Cys Thr
            740                 745                 750

GTG GAA AGG ATC AAG GCT GCA GTA ACG GGG GAA AGT CCC CAA             2594
Val Glu Arg Ile Lys Ala Ala Val Thr Gly Glu Ser Pro Gln
755                 760                 765

TGAGCCTAAG GGCTCCTACA AATCAATGGA ATTGAAGAGG ACTAAGCTTC AGAGGGAGCA   2654

ATGGGATCAA TTACTGGACG TCGGAAGTAG TCAAGAACGC ACCTCAGACA ATCCTTGCCA   2714

CGTGGCGTGT TTCTGTAGTT CTTAAAATAG AGCTTAAATG TAGAGCACTC CACCATGCAA   2774

GGGTGTTGGT TCGGGTATTG ACTCCCCCTT TCTATTTGTT ATTCCCCTCC CTCTCTCTTT   2834

GTACTTCTGC AGACAAGAAG AAAAAAAACT TGTTTTAGCT TCTATTAGTA GCTCTCTTTC   2894

TCTCTCTAGA ATTCCCTCTC TCTCTCTCTC TACTAGATTG ATCACCAACA TATATAAACT   2954

TCATCAAATT TGTGCATTAT CATCCCATGT TGAAGTATTT TGTGAGGGAT TTCATTTGGT   3014

AAAATCAGTA TTTTTTTCTT TTATAAATTT ACAAACATTT CATTCC                 3060

(2) INFORMATION FOR SEQ ID NO:2:

(i) SEQUENCE CHARACTERISTICS:
         (A) LENGTH: 768 amino acids
         (B) TYPE: amino acid
         (D) TOPOLOGY: linear
```

(ii) MOLECULE TYPE: protein (xi) SEQUENCE DESCRIPTION: SEQ ID NO:2:

```
Met Leu Ala Gly Val Met Ile Pro Ala Arg Gln Val Pro Ser Met Ile
 1               5                  10                  15

Gly Arg Asn Ser Ser Ala Leu Thr Leu Ala Gln Ile Asn Ile Leu Glu
                20                  25                  30

Gly Gln Gln Leu Pro Leu Gln His Gln Leu Ala Glu Leu Thr Ala Gln
            35                  40                  45

Ala Thr Thr Thr Ala Glu Ser Asp Met Met Arg Ala Arg Glu Asp Asp
        50                  55                  60

Phe Glu Ser Lys Ser Gly Ser Asp Asn Ile Glu Gly Gly Ser Gly Asp
65                  70                  75                  80

Glu His Asp Pro Asn Gln Arg Pro Arg Lys Lys Arg Tyr His Arg His
                85                  90                  95

Thr Gln His Gln Ile Gln Glu Met Glu Ala Phe Phe Lys Glu Cys Pro
                100                 105                 110

His Pro Asp Asp Lys Gln Arg Lys Ala Leu Ser Lys Glu Leu Gly Leu
            115                 120                 125

Glu Pro Leu Gln Val Lys Phe Trp Phe Gln Asn Lys Arg Thr Gln Met
130                 135                 140

Lys Thr Gln His Asp Arg Gln Glu Asn Ser Gln Leu Arg Ala Glu Asn
145                 150                 155                 160

Asp Lys Leu Arg Asn Glu Asn Leu Arg Tyr Lys Glu Ala Leu Ser Asn
                165                 170                 175

Ala Ser Cys Pro Asn Cys Gly Gly Pro Ala Thr Leu Gly Glu Met Ser
            180                 185                 190

Phe Asp Glu His His Leu Arg Ile Glu Asn Ala Arg Leu Arg Glu Glu
        195                 200                 205

Ile Asp Arg Ile Ser Gly Ile Ala Ala Lys Tyr Val Gly Lys Pro Met
        210                 215                 220

Asn Ser Tyr Pro Leu Leu Ser Pro Thr Leu Pro Ser Arg Ser Ser Leu
225                 230                 235                 240

Asp Leu Gly Val Gly Gly Phe Gly Leu His Ser Pro Thr Met Gly Gly
                245                 250                 255

Asp Met Phe Ser Pro Ala Glu Leu Leu Arg Ser Val Ala Gly Gln Pro
            260                 265                 270

Glu Val Asp Lys Pro Met Val Ile Glu Leu Ala Val Ala Ala Met Glu
        275                 280                 285

Glu Leu Ile Arg Met Ala Gln Leu Gly Glu Pro Leu Trp Thr Ser Ser
        290                 295                 300

Pro Gly Leu Asp Gly Gly Asn Glu Ile Leu Asn Glu Glu Tyr Val
305                 310                 315                 320

Gln Asn Phe Pro Arg Gly Ile Gly Pro Lys Pro Phe Gly Leu Lys Ser
                325                 330                 335

Glu Ala Ser Arg Glu Thr Ala Val Val Ile Met Ser His Val Asn Leu
            340                 345                 350

Val Glu Ile Leu Met Asp Ala Asn Gln Trp Ser Thr Met Phe Ser Gly
        355                 360                 365

Ile Val Ser Arg Gly Met Thr Leu Glu Val Leu Ser Thr Gly Val Ala
        370                 375                 380

Gly Asn Tyr Asn Gly Ala Leu Gln Val Met Thr Ala Glu Phe Gln Val
385                 390                 395                 400

Pro Ser Pro Leu Val Pro Thr Arg Glu Ser Tyr Phe Val Arg Tyr Cys
```

```
                    405                 410                 415
Lys Gln His Pro Asp Gly Thr Trp Ala Val Val Asp Val Ser Leu Asp
            420                 425                 430

Ser Leu Arg Pro Ser Ser Leu Met Met Arg Cys Arg Arg Arg Pro Ser
            435                 440                 445

Gly Cys Leu Ile Gln Glu Met Pro Asn Gly Tyr Ser Lys Val Ile Trp
            450                 455                 460

Val Glu His Phe Glu Val Asp Asp Arg Ser Val His Ser Ile Tyr Lys
465                 470                 475                 480

Pro Leu Val Asn Ser Gly Ile Ala Phe Gly Ala Lys Arg Trp Val Ser
                485                 490                 495

Thr Leu Asp Arg Gln Cys Glu Arg Leu Ala Ser Val Met Ala Ser Ser
                500                 505                 510

Ile Pro Ser Gly Glu Ile Gly Val Ile Thr Thr Ser Glu Gly Arg Lys
                515                 520                 525

Ser Met Leu Lys Leu Ala Glu Arg Met Val Leu Ser Phe Cys Gly Gly
            530                 535                 540

Val Ser Ala Ser Thr Thr His Gln Trp Thr Thr Leu Ser Gly Ser Gly
545                 550                 555                 560

Ala Glu Asp Val Arg Val Met Thr Arg Lys Ser Val Asp Asp Pro Gly
                565                 570                 575

Arg Pro Pro Gly Ile Val Leu Asn Ala Ala Thr Ser Phe Trp Leu Pro
                580                 585                 590

Val Ser Pro Lys Arg Val Phe Asp Phe Leu Arg Asp Glu Ser Ser Arg
                595                 600                 605

Ser Glu Trp Asp Ile Leu Ser Asn Gly Gly Val Val Gln Glu Met Ala
            610                 615                 620

His Ile Ala Asn Gly Arg Asp His Gly Asn Cys Val Ser Leu Leu Arg
625                 630                 635                 640

Val Asn Ser Thr Asn Ser Asn Gln Ser Asn Met Leu Ile Leu Gln Glu
                645                 650                 655

Ser Cys Thr Asp Pro Thr Gly Ser Tyr Val Ile Tyr Ala Pro Val Asp
                660                 665                 670

Val Val Ala Met Asn Val Val Leu Asn Gly Gly Asp Pro Asp Tyr Val
                675                 680                 685

Ala Leu Leu Pro Ser Gly Phe Ala Ile Leu Pro Asp Gly Ser Asn Gly
            690                 695                 700

Val His Gly Gly Gly Ser Gly Ile Gly Glu Val Gly Ser Gly Gly Gly
705                 710                 715                 720

Ser Leu Leu Thr Val Ala Phe Gln Ile Leu Val Asp Ser Ile Pro Thr
                725                 730                 735

Ala Lys Leu Ser Leu Gly Ser Val Ala Thr Val Asn Ser Leu Ile Ala
                740                 745                 750

Cys Thr Val Glu Arg Ile Lys Ala Ala Val Thr Gly Glu Ser Pro Gln
            755                 760                 765

(2) INFORMATION FOR SEQ ID NO:3:

(i) SEQUENCE CHARACTERISTICS:
        (A) LENGTH: 1799 base pairs
        (B) TYPE: nucleic acid
        (C) STRANDEDNESS: single
        (D) TOPOLOGY: linear (ii) MOLECULE TYPE: DNA (genomic)

(ix) FEATURE:
```

5,907,082

33

34

-continued (A) NAME/KEY: unsure
         (B) LOCATION: 19..23

(ix) FEATURE:
         (A) NAME/KEY: CDS
         (B) LOCATION: 291..1571
         (D) OTHER INFORMATION: /note= "clone O40 ovule-specific gene
             encoding a cytochrome P450 monooxygenase
             from pollen tubes of Phalaenopsis"

(xi) SEQUENCE DESCRIPTION: SEQ ID NO:3:

```
CGGCACCACT CCTCTCTGNN NNNCTAATAT CTGGTTAAAA ATGACAATGT CATCCATGGA      60

TTCATCTTCA ATAATATTAA CTTATCTCTC CCCAACACTT TCTCCAGCTA TCGCCGCTTC     120

TATCATCATC ATCTCAGCTC TACTACTCTT TCCCGGCGGT CTGGCGTGGG CCCTTTCCCT     180

CAAGCGCCCA ACATTCTCCG GGCCCACCGG AATTGTTTTT GCTCTCGCCA GCTCTGCTGC     240

TCATAAGTCA CTTGCCGCCC TAGCTCGCTC CGTTCGACGC CCTCCGCCTC ATG GCT       296
                                                         Met Ala
                                                          1

TTC TCG GTC GGC CTC ACT CGC TTC ATC GTT TCA AGC CAC CCG AAA ACC      344
Phe Ser Val Gly Leu Thr Arg Phe Ile Val Ser Ser His Pro Lys Thr
         5                  10                  15

GCA AAA GAG ATT CTT TCA AGC CCA GCC TTC GCT GAT CGG CCC ATT AAA      392
Ala Lys Glu Ile Leu Ser Ser Pro Ala Phe Ala Asp Arg Pro Ile Lys
 20                  25                  30

GAA TCA GCA TAC GAA CTT CTG TTT AAT CGC GCT ATG GGT TTT GCC CCA      440
Glu Ser Ala Tyr Glu Leu Leu Phe Asn Arg Ala Met Gly Phe Ala Pro
 35                  40                  45                  50

TTT GGG GAT TAC TGG AGA AAC CTG AGA AGG ATT TCG TCC ACA TAT CTT      488
Phe Gly Asp Tyr Trp Arg Asn Leu Arg Arg Ile Ser Ser Thr Tyr Leu
                 55                  60                  65

TTC AGT CCG CGG CGA GTT TCA TCG TTC GAG AAG CAA CGG AGT GAG ATT      536
Phe Ser Pro Arg Arg Val Ser Ser Phe Glu Lys Gln Arg Ser Glu Ile
         70                  75                  80

GGC GAA GGA ATG GTG CGG GAT ATG AAA AGA ATG ATG GAG AGA AAT GGA      584
Gly Glu Gly Met Val Arg Asp Met Lys Arg Met Met Glu Arg Asn Gly
 85                  90                  95

GTT GTA GAA GTG AGG AGA ATG TTG CAC TAC GGG TCT TTG AAT AAC ATC      632
Val Val Glu Val Arg Arg Met Leu His Tyr Gly Ser Leu Asn Asn Ile
100                 105                 110

ATG TTG ACT GTT TTT GGG AAA AAG TTT GAT TTT GCA AAG GAT GAG GGG      680
Met Leu Thr Val Phe Gly Lys Lys Phe Asp Phe Ala Lys Asp Glu Gly
115                 120                 125                 130

TTG GAG CTT GAG TTG ATC CTT AAG GAA GGA TAT GAG TTA CTT GGG ATC      728
Leu Glu Leu Glu Leu Ile Leu Lys Glu Gly Tyr Glu Leu Leu Gly Ile
                135                 140                 145

TTC AAC TGG GGT GAT CAT TTG CCT CTT TTG GGA TGG TTA GAT TTG CAA      776
Phe Asn Trp Gly Asp His Leu Pro Leu Leu Gly Trp Leu Asp Leu Gln
        150                 155                 160

GGT GTG AGG AGA AGA TGC AGA ACA CTT GTG GCT AAG GTC AAT GTA TTT      824
Gly Val Arg Arg Arg Cys Arg Thr Leu Val Ala Lys Val Asn Val Phe
        165                 170                 175

GTG AAG AAG ATC ATA GAC GAG CAT AAG AGG AGA GCC AAC GGC GTA GGG      872
Val Lys Lys Ile Ile Asp Glu His Lys Arg Arg Ala Asn Gly Val Gly
180                 185                 190

ATT GAT GAG GGT GAA GGT GAA GAT TTT GTT GAT GTG CTT CTT GGT TTG      920
Ile Asp Glu Gly Glu Gly Glu Asp Phe Val Asp Val Leu Leu Gly Leu
195                 200                 205                 210

GAG GAG AAA GAT AGA CTC TCA GAA TCT GAT ATG GTC GCA GTT CTT TGG      968
Glu Glu Lys Asp Arg Leu Ser Glu Ser Asp Met Val Ala Val Leu Trp
                215                 220                 225
```

```
GAA ATG ATC TTT AGA GGA ACT GAT ACT GTT GCC ATC CTA TTG GAA TGG      1016
Glu Met Ile Phe Arg Gly Thr Asp Thr Val Ala Ile Leu Leu Glu Trp
        230                 235                 240

ACG TTG GCT AGA ATG GTT CTT CAT CCT GAT ATT CAA TCG AAG GCA CAA      1064
Thr Leu Ala Arg Met Val Leu His Pro Asp Ile Gln Ser Lys Ala Gln
            245                 250                 255

GTT GAG ATT GAT TCT GTC GTT GAC TCT TCA AGG CCA GTA TTG GAT TCT      1112
Val Glu Ile Asp Ser Val Val Asp Ser Ser Arg Pro Val Leu Asp Ser
260                 265                 270

GAT ATC CAA CGA CTT CCT TAT CTC CAA TCT ATA GTA AAA GAA ACC CTT      1160
Asp Ile Gln Arg Leu Pro Tyr Leu Gln Ser Ile Val Lys Glu Thr Leu
275                 280                 285                 290

CGA ATG CAT CCT CCT GGG CCT CTA TTG TCA TGG GCT CGC CTA GCT ATC      1208
Arg Met His Pro Pro Gly Pro Leu Leu Ser Trp Ala Arg Leu Ala Ile
                295                 300                 305

CAT GAC GTT CCT GTT GAT GGT CAC ATG ATT CCT GCT GGG ACG ACT GCA      1256
His Asp Val Pro Val Asp Gly His Met Ile Pro Ala Gly Thr Thr Ala
            310                 315                 320

ATG GTG AAC ATG TGG GCA ATA ACA CAT GAC GAA TGC AAC TGG GCT GAG      1304
Met Val Asn Met Trp Ala Ile Thr His Asp Glu Cys Asn Trp Ala Glu
325                 330                 335

CCT AAC AAA TTC AAT CCT GAT CGA TTC ATC GAT GAA GAT GTC AAT ATT      1352
Pro Asn Lys Phe Asn Pro Asp Arg Phe Ile Asp Glu Asp Val Asn Ile
340                 345                 350

CTT GGT TCC GAT TTA AGG TTG GCA CCC TTT GGC TCC GGT AAA AGA GTT      1400
Leu Gly Ser Asp Leu Arg Leu Ala Pro Phe Gly Ser Gly Lys Arg Val
355                 360                 365                 370

TGC CCT GGC AAA ACG ATG GCA TTG GCT GCA GTT CAT CTT TGG TTG GCT      1448
Cys Pro Gly Lys Thr Met Ala Leu Ala Ala Val His Leu Trp Leu Ala
                375                 380                 385

CAG TTG CTG AAA AGC TTC AAA TTG CTT CCT TCG AGA AAT GGT GTA GAT      1496
Gln Leu Leu Lys Ser Phe Lys Leu Leu Pro Ser Arg Asn Gly Val Asp
            390                 395                 400

TTG TCT GAG TGC CTA AAG ATG TCT CTC GAG ATG AAG AAT CCT TTG GTA      1544
Leu Ser Glu Cys Leu Lys Met Ser Leu Glu Met Lys Asn Pro Leu Val
        405                 410                 415

TGT GTG GCT GTT CCA AGG TTC GAG TAGTCCTGCT AAGATGACGT CTAGTTATAA     1598
Cys Val Ala Val Pro Arg Phe Glu
420                 425

GAAATTTGTT CTTTGCAAAT TGTGGCCAAC ATAAATGATT TCGTAAGCTA GCAACTTATG    1658

GATAATGTCG GTACATGTTC GTTTAAAGTG TCAACTTTGT TTGGTTGAAT TTTAAAATTT    1718

GACATTGTAA TAAAGATTCT CTGGTTCTAT GTAAATATTG TAATTCAGCT TATAATATAA    1778

GAAAGAAATG AATTTGTTGC T                                              1799

(2) INFORMATION FOR SEQ ID NO:4:

(i) SEQUENCE CHARACTERISTICS:
         (A) LENGTH: 426 amino acids
         (B) TYPE: amino acid
         (D) TOPOLOGY: linear (ii) MOLECULE TYPE: protein (xi) SEQUENCE DESCRIPTION: SEQ ID NO:4:

Met Ala Phe Ser Val Gly Leu Thr Arg Phe Ile Val Ser Ser His Pro
1               5                   10                  15

Lys Thr Ala Lys Glu Ile Leu Ser Ser Pro Ala Phe Ala Asp Arg Pro
            20                  25                  30

Ile Lys Glu Ser Ala Tyr Glu Leu Leu Phe Asn Arg Ala Met Gly Phe
        35                  40                  45
```

```
Ala Pro Phe Gly Asp Tyr Trp Arg Asn Leu Arg Arg Ile Ser Ser Thr
         50                  55                  60

Tyr Leu Phe Ser Pro Arg Arg Val Ser Ser Phe Glu Lys Gln Arg Ser
 65                  70                  75                  80

Glu Ile Gly Glu Gly Met Val Arg Asp Met Lys Arg Met Met Glu Arg
                 85                  90                  95

Asn Gly Val Val Glu Val Arg Arg Met Leu His Tyr Gly Ser Leu Asn
            100                 105                 110

Asn Ile Met Leu Thr Val Phe Gly Lys Lys Phe Asp Phe Ala Lys Asp
        115                 120                 125

Glu Gly Leu Glu Leu Glu Leu Ile Leu Lys Glu Gly Tyr Glu Leu Leu
    130                 135                 140

Gly Ile Phe Asn Trp Gly Asp His Leu Pro Leu Leu Gly Trp Leu Asp
145                 150                 155                 160

Leu Gln Gly Val Arg Arg Arg Cys Arg Thr Leu Val Ala Lys Val Asn
                165                 170                 175

Val Phe Val Lys Lys Ile Ile Asp Glu His Lys Arg Arg Ala Asn Gly
            180                 185                 190

Val Gly Ile Asp Glu Gly Glu Gly Asp Phe Val Asp Val Leu Leu
        195                 200                 205

Gly Leu Glu Glu Lys Asp Arg Leu Ser Glu Ser Asp Met Val Ala Val
    210                 215                 220

Leu Trp Glu Met Ile Phe Arg Gly Thr Asp Thr Val Ala Ile Leu Leu
225                 230                 235                 240

Glu Trp Thr Leu Ala Arg Met Val Leu His Pro Asp Ile Gln Ser Lys
                245                 250                 255

Ala Gln Val Glu Ile Asp Ser Val Val Asp Ser Ser Arg Pro Val Leu
            260                 265                 270

Asp Ser Asp Ile Gln Arg Leu Pro Tyr Leu Gln Ser Ile Val Lys Glu
        275                 280                 285

Thr Leu Arg Met His Pro Pro Gly Pro Leu Leu Ser Trp Ala Arg Leu
    290                 295                 300

Ala Ile His Asp Val Pro Val Asp Gly His Met Ile Pro Ala Gly Thr
305                 310                 315                 320

Thr Ala Met Val Asn Met Trp Ala Ile Thr His Asp Glu Cys Asn Trp
                325                 330                 335

Ala Glu Pro Asn Lys Phe Asn Pro Asp Arg Phe Ile Asp Glu Asp Val
            340                 345                 350

Asn Ile Leu Gly Ser Asp Leu Arg Leu Ala Pro Phe Gly Ser Gly Lys
        355                 360                 365

Arg Val Cys Pro Gly Lys Thr Met Ala Leu Ala Val His Leu Trp
    370                 375                 380

Leu Ala Gln Leu Leu Lys Ser Phe Lys Leu Leu Pro Ser Arg Asn Gly
385                 390                 395                 400

Val Asp Leu Ser Glu Cys Leu Lys Met Ser Leu Glu Met Lys Asn Pro
                405                 410                 415

Leu Val Cys Val Ala Val Pro Arg Phe Glu
            420                 425

(2) INFORMATION FOR SEQ ID NO:5:

(i) SEQUENCE CHARACTERISTICS:
        (A) LENGTH: 782 base pairs
        (B) TYPE: nucleic acid
        (C) STRANDEDNESS: single
```

(D) TOPOLOGY: linear (ii) MOLECULE TYPE: DNA (genomic)

(ix) FEATURE:
    (A) NAME/KEY: CDS
    (B) LOCATION: 79..405
    (D) OTHER INFORMATION: /note= "clone O108 ovule-specific gene
        from Phalaenopsis"

(xi) SEQUENCE DESCRIPTION: SEQ ID NO:5:

```
AATTCGGCAC GAGTATGAAA GGAGAAAGGT GACTTTGAAG AGCTCGGCGA AGAATTCTTG            60

GTAGAAGAAG CCGTGGCA ATG GAG TCT CGG ATG ATC CGT TAC ATG ATT TGG            111
                    Met Glu Ser Arg Met Ile Arg Tyr Met Ile Trp
                     1               5                  10

GAT GGA CTA GCA GGT GAC GTG ATT GAA CTC CCT GGC GTG AAG GGT AAG           159
Asp Gly Leu Ala Gly Asp Val Ile Glu Leu Pro Gly Val Lys Gly Lys
             15                  20                  25

TTT CTA TCT ATG ATT CTT GAT TTT TGC AAG AAA CGT GTT GCA TGG GCT           207
Phe Leu Ser Met Ile Leu Asp Phe Cys Lys Lys Arg Val Ala Trp Ala
         30                  35                  40

GCT GGC GGC GAT GGG ACG TTG GAA GGC TTG AAA TCT GAT TTT GTG AAT           255
Ala Gly Gly Asp Gly Thr Leu Glu Gly Leu Lys Ser Asp Phe Val Asn
     45                  50                  55

GTT GAT TTG GGC ACA CTG ATC CAT CTT GGT GCA GCA AGC TTT TAT CTG           303
Val Asp Leu Gly Thr Leu Ile His Leu Gly Ala Ala Ser Phe Tyr Leu
 60                  65                  70                  75

AAA ACA AAT GAT TTG GTT GAT TTG ACC TCT CAA ACT TTA GCA AAT CGG           351
Lys Thr Asn Asp Leu Val Asp Leu Thr Ser Gln Thr Leu Ala Asn Arg
                 80                  85                  90

ATT CAG GGG AAG ACT ATT GAA GAG GTT TGC AGG GCC TTG AAC CCT GAA           399
Ile Gln Gly Lys Thr Ile Glu Glu Val Cys Arg Ala Leu Asn Pro Glu
             95                 100                 105

GAA TAAAAGGAGA TTCAGATGGA GAATTCGTGG ACATTTGAGT GAAATGATGG                452
Glu

TGGTGCTCTC TCTCTCTCTC CCCCCACACC TTCGCCCTAT ATTTACTATG AGTCTCTTTA          512

GTTTTCTATT TTATTTGATC ATGTTGAGTC TAGTGTGTTC TCTATACTTA TTTGAAAGTG          572

ATGATTGTCT TTTATTTGCT GTTGCAAGTT TAGGGTAAGA AAGTTGAAAT AACATAACAT          632

ATGTATCTCT CGAAACACTT TTGGTGCCAA CTTAAAGCTA CCATCTATAT AATTTTGACA          692

CTTGTGTATT AATATCGTTG GGTCCTTTCA ACAACTTGTG TTTAGCTATG TAATTTCGCT          752

ATTTGTGTTT ACATATTACA TCTATTTTCT                                          782
```

(2) INFORMATION FOR SEQ ID NO:6:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:6:

```
Met Glu Ser Arg Met Ile Arg Tyr Met Ile Trp Asp Gly Leu Ala Gly
 1               5                  10                  15

Asp Val Ile Glu Leu Pro Gly Val Lys Gly Lys Phe Leu Ser Met Ile
             20                  25                  30

Leu Asp Phe Cys Lys Lys Arg Val Ala Trp Ala Ala Gly Gly Asp Gly
         35                  40                  45

Thr Leu Glu Gly Leu Lys Ser Asp Phe Val Asn Val Asp Leu Gly Thr
     50                  55                  60
```

```
        Leu Ile His Leu Gly Ala Ala Ser Phe Tyr Leu Lys Thr Asn Asp Leu
         65                  70                  75                  80

Val Asp Leu Thr Ser Gln Thr Leu Ala Asn Arg Ile Gln Gly Lys Thr
                         85                  90                  95

Ile Glu Glu Val Cys Arg Ala Leu Asn Pro Glu Glu
                        100                 105

(2) INFORMATION FOR SEQ ID NO:7:

(i) SEQUENCE CHARACTERISTICS:
          (A) LENGTH: 850 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: CDS
          (B) LOCATION: 1..573
          (D) OTHER INFORMATION: /note= "clone O126 ovule-specific gene
              from Phalaenopsis"

(xi) SEQUENCE DESCRIPTION: SEQ ID NO:7:

TGC CGC CAT GTA AAA ACC TTG CAA TTC TAC TTT TGC TTA GCA TTA GTG         48
Cys Arg His Val Lys Thr Leu Gln Phe Tyr Phe Cys Leu Ala Leu Val
  1               5                  10                  15

TTT GCC TTT CTT TGC GAG GCT TTG ATG GAT ATT GGG GAG TCA AAA TCG         96
Phe Ala Phe Leu Cys Glu Ala Leu Met Asp Ile Gly Glu Ser Lys Ser
                 20                  25                  30

ACT CTT AGT TAC TCC CCG CCA CCA GAC AAT ACT AGA CTA GGG GTA GGG        144
Thr Leu Ser Tyr Ser Pro Pro Pro Asp Asn Thr Arg Leu Gly Val Gly
             35                  40                  45

CAT GGT TCA GGC AAC AGC AGT CGC CAC AAT AGT GGG ATC GGT GTT GGC        192
His Gly Ser Gly Asn Ser Ser Arg His Asn Ser Gly Ile Gly Val Gly
         50                  55                  60

CGT GGA GGA TTT GAT GGA GGC GAT GGC AGC AGC GGA GTA GTT GGT GGA        240
Arg Gly Gly Phe Asp Gly Gly Asp Gly Ser Ser Gly Val Val Gly Gly
 65                  70                  75                  80

GGG GTT GGC AAC GGT GAT CAA CCC TGG GGC GGT GAT CAA CCC ATT GGA        288
Gly Val Gly Asn Gly Asp Gln Pro Trp Gly Gly Asp Gln Pro Ile Gly
                 85                  90                  95

AGC GGC GAT GGC GAC GAC AAT GGT AAT GAT GGT AAT GAT AAT GGT GAA        336
Ser Gly Asp Gly Asp Asp Asn Gly Asn Asp Gly Asn Asp Asn Gly Glu
             100                 105                 110

GGA GAC GGT GAT CAA CCC ATC GGA AGC GGC AAT GAC GAC GGC AAT GGT        384
Gly Asp Gly Asp Gln Pro Ile Gly Ser Gly Asn Asp Asp Gly Asn Gly
         115                 120                 125

AAT GGT AAT GAT GGA GAA GGA GAC GGT GAT CAA CCC ATG CGG GGC GGC        432
Asn Gly Asn Asp Gly Glu Gly Asp Gly Asp Gln Pro Met Arg Gly Gly
 130                 135                 140

AAT GAC GAC GGC AAT GGT AAT AAT GAT GGT GGA GAA GGA ACT GGT GAT        480
Asn Asp Asp Gly Asn Gly Asn Asn Asp Gly Gly Glu Gly Thr Gly Asp
145                 150                 155                 160

GAA CCA ATC GGG GGC GGT GAC GGT GGT GGC GAC GAA GGA TAT GGC GGT        528
Glu Pro Ile Gly Gly Gly Asp Gly Gly Gly Asp Glu Gly Tyr Gly Gly
                 165                 170                 175

GGC GAT GAT GGC GGC GAT GGT GGC GGC GGT GAT GGT CGC CGT                570
Gly Asp Asp Gly Gly Asp Gly Gly Gly Gly Asp Gly Arg Arg
             180                 185                 190

TAAAGAGTGT TCAAAAGCAG GAGGTGGCTG CAGCCATTAT CTCGGTGGTC GTGGTCACGA       630

GGCAACAGTT GAGGTTTATG AAAGTGGCCT AAGTCCTGCT TCTGTTCTAC TTAACATTAT       690
```

```
AGCTATGGTT ACTAAGAATA AGACCCGTTG ATGGTCATTA TTGTATTCTG GGGTTTTCTA      750

GTTAGATTAA AAAGTCTATA ATAATGTGAA ATTATAATAT GGGTTGTAAT AGAAATCATA      810

TTTGGTATTA TCATGCAATG GAGAACGATG TCACTTTTAT                            850
```

(2) INFORMATION FOR SEQ ID NO:8:

(i) SEQUENCE CHARACTERISTICS:
        (A) LENGTH: 190 amino acids
        (B) TYPE: amino acid
        (D) TOPOLOGY: linear (ii) MOLECULE TYPE: protein (xi) SEQUENCE DESCRIPTION: SEQ ID NO:8:

```
Cys Arg His Val Lys Thr Leu Gln Phe Tyr Phe Cys Leu Ala Leu Val
 1               5                  10                  15

Phe Ala Phe Leu Cys Glu Ala Leu Met Asp Ile Gly Glu Ser Lys Ser
            20                  25                  30

Thr Leu Ser Tyr Ser Pro Pro Asp Asn Thr Arg Leu Gly Val Gly
        35                  40                  45

His Gly Ser Gly Asn Ser Ser Arg His Asn Ser Gly Ile Gly Val Gly
    50                  55                  60

Arg Gly Gly Phe Asp Gly Gly Asp Gly Ser Ser Gly Val Val Gly Gly
65                  70                  75                  80

Gly Val Gly Asn Gly Asp Gln Pro Trp Gly Gly Asp Gln Pro Ile Gly
                85                  90                  95

Ser Gly Asp Gly Asp Asp Asn Gly Asn Asp Gly Asn Asp Asn Gly Glu
            100                 105                 110

Gly Asp Gly Asp Gln Pro Ile Gly Ser Gly Asn Asp Gly Asn Gly
        115                 120                 125

Asn Gly Asn Asp Gly Glu Gly Asp Gly Asp Gln Pro Met Arg Gly Gly
    130                 135                 140

Asn Asp Asp Gly Asn Gly Asn Asn Asp Gly Gly Glu Gly Thr Gly Asp
145                 150                 155                 160

Glu Pro Ile Gly Gly Gly Asp Gly Gly Gly Asp Glu Gly Tyr Gly Gly
                165                 170                 175

Gly Asp Asp Gly Gly Asp Gly Gly Gly Gly Asp Gly Arg Arg
            180                 185                 190
```

(2) INFORMATION FOR SEQ ID NO:9:

(i) SEQUENCE CHARACTERISTICS:
        (A) LENGTH: 1334 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 12..1091
        (D) OTHER INFORMATION: /note= "clone O141 ovule-specific gene
            from Phalaenopsis"

(xi) SEQUENCE DESCRIPTION: SEQ ID NO:9:

```
GCACGAGGAA A ATG AAG CTC TTT TCT CTA ATC TTG GTC GCA TCA TTC CTT      50
            Met Lys Leu Phe Ser Leu Ile Leu Val Ala Ser Phe Leu
             1               5                  10

GCA TCA GTA GCT GCC ACA GCC ATC GAC ATA GCT GAC AAG GAT TTA GAG       98
Ala Ser Val Ala Ala Thr Ala Ile Asp Ile Ala Asp Lys Asp Leu Glu
```

-continued

```
              15                      20                      25
ACG GAA GAC AGT CTC TGG AAT CTC TAC GAG CGA TGG AGA AGC CAT CAC      146
Thr Glu Asp Ser Leu Trp Asn Leu Tyr Glu Arg Trp Arg Ser His His
        30                      35                      40                  45

ACT GTC TCG AGA GAC CTC GAT GAG AAA CAA AAG CGT TTT AAT GTT TTT      194
Thr Val Ser Arg Asp Leu Asp Glu Lys Gln Lys Arg Phe Asn Val Phe
                    50                      55                      60

AAA GAG AAC CCT CGC TAC ATC CAC GAC TTC AAC AAA CGC AAA GAC ATC      242
Lys Glu Asn Pro Arg Tyr Ile His Asp Phe Asn Lys Arg Lys Asp Ile
                65                      70                      75

CCT TAC AAG CTC CGC CTC AAC AAG TTT GCC GAT TTA ACC AAT CAT GAA      290
Pro Tyr Lys Leu Arg Leu Asn Lys Phe Ala Asp Leu Thr Asn His Glu
            80                      85                      90

TTC CGC TCC ACT TAT GCA GGA TCA CGC ATA AAC CAC CAC CGC TCG CTC      338
Phe Arg Ser Thr Tyr Ala Gly Ser Arg Ile Asn His His Arg Ser Leu
        95                      100                     105

CGC GGT TCC AGA CGC GGC GGC GCC ACA AAC TCA TTC ATG TAT CAG AGC      386
Arg Gly Ser Arg Arg Gly Gly Ala Thr Asn Ser Phe Met Tyr Gln Ser
110                     115                     120                 125

CTT GAT AGT CGT AGT CTT CCT GCC TCC ATA GAT TGG CGG CAA AAA GGC      434
Leu Asp Ser Arg Ser Leu Pro Ala Ser Ile Asp Trp Arg Gln Lys Gly
                130                     135                     140

GCC GTC ACG GCT GTG AAG GAC CAA GGC CAA TGC GGG AGT TGC TGG GCG      482
Ala Val Thr Ala Val Lys Asp Gln Gly Gln Cys Gly Ser Cys Trp Ala
                145                     150                     155

TTC TCG ACG GTG GCT GCT GTG GAG GGA ATA AAC CAA ATC AAG ACG AAA      530
Phe Ser Thr Val Ala Ala Val Glu Gly Ile Asn Gln Ile Lys Thr Lys
                160                     165                     170

AAG TTG CTT TCA TTG TCG GAG CAA GAA CTT ATT GAC TGC GAC ACG GAC      578
Lys Leu Leu Ser Leu Ser Glu Gln Glu Leu Ile Asp Cys Asp Thr Asp
175                     180                     185

GAG AAT AAT GGA TGC AAC GGA GGT CTA ATG GAT TAT GCT TTC GAC TTC      626
Glu Asn Asn Gly Cys Asn Gly Gly Leu Met Asp Tyr Ala Phe Asp Phe
190                     195                     200                 205

ATC AAG AAA AAT GGA GGA ATT TCT TCC GAA GCT GAG TAT CCT TAC GCC      674
Ile Lys Lys Asn Gly Gly Ile Ser Ser Glu Ala Glu Tyr Pro Tyr Ala
                210                     215                     220

GCA GAA GAT AGT TAC TGT GCC ACT GAG AAG AAA TCT CAT GTG GTT TCC      722
Ala Glu Asp Ser Tyr Cys Ala Thr Glu Lys Lys Ser His Val Val Ser
            225                     230                     235

ATT GAC GGG CAC GAA GAT GTC CCT GCA AAC GAC GAG GAC TCT TTG TTG      770
Ile Asp Gly His Glu Asp Val Pro Ala Asn Asp Glu Asp Ser Leu Leu
        240                     245                     250

AAA GCT GTG GCG AAT CAG CCT GTA TCA ATC GCC ATT GAA GCT AGT GGC      818
Lys Ala Val Ala Asn Gln Pro Val Ser Ile Ala Ile Glu Ala Ser Gly
        255                     260                     265

TAT GAT TTT CAG TTC TAC TCC GAG GGA GTT TTC ACA GGC AGG TCT GGC      866
Tyr Asp Phe Gln Phe Tyr Ser Glu Gly Val Phe Thr Gly Arg Ser Gly
270                     275                     280                 285

ACA GAA TTG GAT CAT GGG GTT GCA ATC GTG GGA TAC GGG AAA ACA CAG      914
Thr Glu Leu Asp His Gly Val Ala Ile Val Gly Tyr Gly Lys Thr Gln
                290                     295                     300

CAA GGA ACT AAG TAT TGG ATC GTG AGG AAC TCA TGG GGG GCG GAG TGG      962
Gln Gly Thr Lys Tyr Trp Ile Val Arg Asn Ser Trp Gly Ala Glu Trp
            305                     310                     315

GGG GAG AAA GGC TAC ATA AGA ATC TCC GCG GCC TCA GAT TCC AAG CGC      1010
Gly Glu Lys Gly Tyr Ile Arg Ile Ser Ala Ala Ser Asp Ser Lys Arg
                320                     325                     330

TTG TGC GGC CTA GCA ATG GAG GCT TCT TAT CCA ATC AAA ACT TCT CCC      1058
Leu Cys Gly Leu Ala Met Glu Ala Ser Tyr Pro Ile Lys Thr Ser Pro
```

```
                         335                 340                 345
AAT CCT TCG CAC AAG AGC AGG GAT GAA CTC TGACTACAAA TATTGGCTTT       1108
Asn Pro Ser His Lys Ser Arg Asp Glu Leu
350                 355

ATGGATTCAA AATAAGGATA TAAGTTGGTT AGGAAAATTG TGATTTTTAT CTTGTTTGTC   1168

TTTGTTTGAT GTAATTTATA AATCAAATGT AGTTTTAATT GTTGCATTAC TGTCCTGTAT   1228

CTGACATGAA TTAAATTACT TTTAGTTTCA TCCTTGTAAA TTTTTTTATG TTCTCTTCTG   1288

TTTTAAGAAA GCAAAAGCCT TTTACTTGCA AGTAACATTT TATGCT                  1334

(2) INFORMATION FOR SEQ ID NO:10:

(i) SEQUENCE CHARACTERISTICS:
        (A) LENGTH: 359 amino acids
        (B) TYPE: amino acid
        (D) TOPOLOGY: linear (ii) MOLECULE TYPE: protein (xi) SEQUENCE DESCRIPTION: SEQ ID NO:10:

Met Lys Leu Phe Ser Leu Ile Leu Val Ala Ser Phe Leu Ala Ser Val
  1               5                  10                  15

Ala Ala Thr Ala Ile Asp Ile Ala Asp Lys Asp Leu Glu Thr Glu Asp
                 20                  25                  30

Ser Leu Trp Asn Leu Tyr Glu Arg Trp Arg Ser His His Thr Val Ser
         35                  40                  45

Arg Asp Leu Asp Glu Lys Gln Lys Arg Phe Asn Val Phe Lys Glu Asn
     50                  55                  60

Pro Arg Tyr Ile His Asp Phe Asn Lys Arg Lys Asp Ile Pro Tyr Lys
 65                  70                  75                  80

Leu Arg Leu Asn Lys Phe Ala Asp Leu Thr Asn His Glu Phe Arg Ser
                 85                  90                  95

Thr Tyr Ala Gly Ser Arg Ile Asn His His Arg Ser Leu Arg Gly Ser
            100                 105                 110

Arg Arg Gly Gly Ala Thr Asn Ser Phe Met Tyr Gln Ser Leu Asp Ser
        115                 120                 125

Arg Ser Leu Pro Ala Ser Ile Asp Trp Arg Gln Lys Gly Ala Val Thr
130                 135                 140

Ala Val Lys Asp Gln Gly Gln Cys Gly Ser Cys Trp Ala Phe Ser Thr
145                 150                 155                 160

Val Ala Ala Val Glu Gly Ile Asn Gln Ile Lys Thr Lys Lys Leu Leu
                165                 170                 175

Ser Leu Ser Glu Gln Glu Leu Ile Asp Cys Asp Thr Asp Glu Asn Asn
            180                 185                 190

Gly Cys Asn Gly Gly Leu Met Asp Tyr Ala Phe Asp Phe Ile Lys Lys
        195                 200                 205

Asn Gly Gly Ile Ser Ser Glu Ala Glu Tyr Pro Tyr Ala Ala Glu Asp
    210                 215                 220

Ser Tyr Cys Ala Thr Glu Lys Lys Ser His Val Val Ser Ile Asp Gly
225                 230                 235                 240

His Glu Asp Val Pro Ala Asn Asp Glu Asp Ser Leu Leu Lys Ala Val
                245                 250                 255

Ala Asn Gln Pro Val Ser Ile Ala Ile Glu Ala Ser Gly Tyr Asp Phe
            260                 265                 270

Gln Phe Tyr Ser Glu Gly Val Phe Thr Gly Arg Ser Gly Thr Glu Leu
        275                 280                 285
```

```
Asp His Gly Val Ala Ile Val Gly Tyr Gly Lys Thr Gln Gln Gly Thr
    290                 295                 300

Lys Tyr Trp Ile Val Arg Asn Ser Trp Gly Ala Glu Trp Gly Glu Lys
305                 310                 315                 320

Gly Tyr Ile Arg Ile Ser Ala Ala Ser Asp Ser Lys Arg Leu Cys Gly
                325                 330                 335

Leu Ala Met Glu Ala Ser Tyr Pro Ile Lys Thr Ser Pro Asn Pro Ser
            340                 345                 350

His Lys Ser Arg Asp Glu Leu
        355
```

(2) INFORMATION FOR SEQ ID NO:11:

(i) SEQUENCE CHARACTERISTICS:
        (A) LENGTH: 2939 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 336..2492
        (D) OTHER INFORMATION: /note= "clone A20 ovule-specific gene
            from Arabidopsis"

(xi) SEQUENCE DESCRIPTION: SEQ ID NO:11:

```
GTTTTTTCTT CTGAAGAGTG ATATATATTC TACCTTTCTC TGGTTAAAGA AACTCCCTGA      60

ATCCACCGGT TATGTCTTGA CCGGCTTTAA GCCTATAAAC TGATGCCCTA AGACACCTTT     120

TTAGGTTTCT CAATAATTCT CCGCATCTAT CTTTTCTTCT CCACAAGTAA GGGAACCAGA     180

AAACCAGGGA AGAATCCGAG CAAGCTAGGG TTTCATTGTG TGCACAAAAT GGGATATACA     240

GGCAGAAGAA AATCGAGATA AATCAACTAA ATGATTTGGA TAATCATCTT GAAGATTTGA     300

AGGATTTCGA GACTAAGTCC GGCGCAGAAG TCACC ATG GAG AAT CCT TTA GAA        353
                                       Met Glu Asn Pro Leu Glu
                                         1               5

GAA GAG CTT CAA GAT CCT AAT CAG CGT CCC AAC AAA AAG AAG CGT TAC       401
Glu Glu Leu Gln Asp Pro Asn Gln Arg Pro Asn Lys Lys Lys Arg Tyr
        10                  15                  20

CAC CGT CAC ACA CAA CGC CAG ATT CAA GAG CTA GAG TCG TTC TTC AAG       449
His Arg His Thr Gln Arg Gln Ile Gln Glu Leu Glu Ser Phe Phe Lys
    25                  30                  35

GAA TGT CCT CAT CCA GAC GAT AAG CAA AGA AAG GAG CTG AGT CGC GAG       497
Glu Cys Pro His Pro Asp Asp Lys Gln Arg Lys Glu Leu Ser Arg Glu
40                  45                  50

CTA AGC TTA GAA CCT CTT CAA GTC AAG TTC TGG TTC CAA AAC AAA CGC       545
Leu Ser Leu Glu Pro Leu Gln Val Lys Phe Trp Phe Gln Asn Lys Arg
55                  60                  65                  70

ACT CAA ATG AAG GCA CAA CAT GAG AGG CAC GAG AAC CAG ATA CTG AAG       593
Thr Gln Met Lys Ala Gln His Glu Arg His Glu Asn Gln Ile Leu Lys
                75                  80                  85

TCA GAA AAT GAC AAG CTC CGA GCA GAG AAC AAT AGG TAC AAG GAT GCT       641
Ser Glu Asn Asp Lys Leu Arg Ala Glu Asn Asn Arg Tyr Lys Asp Ala
        90                  95                 100

CTA AGC AAC GCA ACA TGC CCA AAC TGT GGT GGT CCG GCA GCT ATA GGA       689
Leu Ser Asn Ala Thr Cys Pro Asn Cys Gly Gly Pro Ala Ala Ile Gly
    105                 110                 115

GAA ATG TCC TTC GAC GAA CAG CAT TTA AGG ATC GAA AAT GCT CGT TTA       737
Glu Met Ser Phe Asp Glu Gln His Leu Arg Ile Glu Asn Ala Arg Leu
120                 125                 130
```

| | | | | | | | | | | | | | | | | |
|---|---|---|---|---|---|---|---|---|---|---|---|---|---|---|---|---|
| CGC | GAA | GAG | ATT | GAC | AGA | ATC | TCT | GCC | ATA | GCT | GCT | AAA | TAC | GTA | GGG | 785 |
| Arg | Glu | Glu | Ile | Asp | Arg | Ile | Ser | Ala | Ile | Ala | Ala | Lys | Tyr | Val | Gly | |
| 135 | | | | 140 | | | | 145 | | | | | | | 150 | |

| | | | | | | | | | | | | | | |
|---|---|---|---|---|---|---|---|---|---|---|---|---|---|---|
| AAG | CCT | TTA | ATG | GCT | AAT | TCC | TCT | TCT | TTC | CCT | CAG | CTC | TCT | TCT | TCA | 833 |
| Lys | Pro | Leu | Met | Ala | Asn | Ser | Ser | Ser | Phe | Pro | Gln | Leu | Ser | Ser | Ser | |
| | | | | 155 | | | | | 160 | | | | | 165 | | |

| CAC | CAC | ATT | CCC | TCG | CGC | TCG | CTT | GAT | CTT | GAA | GTT | GGG | AAC | TTT | GGG | 881 |
|---|---|---|---|---|---|---|---|---|---|---|---|---|---|---|---|---|
| His | His | Ile | Pro | Ser | Arg | Ser | Leu | Asp | Leu | Glu | Val | Gly | Asn | Phe | Gly | |
| | | | 170 | | | | | 175 | | | | | 180 | | | |

| AAC | AAT | AAC | AAT | AGC | CAC | ACT | GGT | TTC | GTT | GGG | GAA | ATG | TTT | GGA | AGC | 929 |
|---|---|---|---|---|---|---|---|---|---|---|---|---|---|---|---|---|
| Asn | Asn | Asn | Asn | Ser | His | Thr | Gly | Phe | Val | Gly | Glu | Met | Phe | Gly | Ser | |
| | | | 185 | | | | | 190 | | | | | 195 | | | |

| AGC | GAC | ATT | TTG | AGG | TCG | GTT | TCG | ATA | CCT | TCT | GAG | GCT | GAT | AAG | CCT | 977 |
|---|---|---|---|---|---|---|---|---|---|---|---|---|---|---|---|---|
| Ser | Asp | Ile | Leu | Arg | Ser | Val | Ser | Ile | Pro | Ser | Glu | Ala | Asp | Lys | Pro | |
| | | 200 | | | | | 205 | | | | | 210 | | | | |

| ATG | ATT | GTT | GAG | TTA | GCT | GTT | GCA | GCA | ATG | GAA | GAG | CTT | GTG | AGA | ATG | 1025 |
|---|---|---|---|---|---|---|---|---|---|---|---|---|---|---|---|---|
| Met | Ile | Val | Glu | Leu | Ala | Val | Ala | Ala | Met | Glu | Glu | Leu | Val | Arg | Met | |
| 215 | | | | 220 | | | | 225 | | | | | | | 230 | |

| GCT | CAA | ACT | GGT | GAT | CCC | TTA | TGG | GTT | TCA | AGC | GAT | AAT | TCT | GTT | GAG | 1073 |
|---|---|---|---|---|---|---|---|---|---|---|---|---|---|---|---|---|
| Ala | Gln | Thr | Gly | Asp | Pro | Leu | Trp | Val | Ser | Ser | Asp | Asn | Ser | Val | Glu | |
| | | | | 235 | | | | | 240 | | | | | 245 | | |

| ATT | CTC | AAT | GAA | GAA | GAG | TAT | TTT | AGG | ACG | TTT | CCT | AGA | GGA | ATT | GGA | 1121 |
|---|---|---|---|---|---|---|---|---|---|---|---|---|---|---|---|---|
| Ile | Leu | Asn | Glu | Glu | Glu | Tyr | Phe | Arg | Thr | Phe | Pro | Arg | Gly | Ile | Gly | |
| | | | 250 | | | | | 255 | | | | | 260 | | | |

| CCG | AAA | CCT | ATC | GGT | TTG | AGA | TCA | GAA | GCT | TCA | AGA | GAG | TCT | ACT | GTT | 1169 |
|---|---|---|---|---|---|---|---|---|---|---|---|---|---|---|---|---|
| Pro | Lys | Pro | Ile | Gly | Leu | Arg | Ser | Glu | Ala | Ser | Arg | Glu | Ser | Thr | Val | |
| | | 265 | | | | | 270 | | | | | 275 | | | | |

| GTT | ATC | ATG | AAT | CAT | ATC | AAT | CTC | ATT | GAG | ATT | CTA | ATG | GAT | GTG | AAT | 1217 |
|---|---|---|---|---|---|---|---|---|---|---|---|---|---|---|---|---|
| Val | Ile | Met | Asn | His | Ile | Asn | Leu | Ile | Glu | Ile | Leu | Met | Asp | Val | Asn | |
| | 280 | | | | | 285 | | | | | 290 | | | | | |

| CAA | TGG | TCT | AGT | GTG | TTC | TGC | GGG | ATT | GTA | TCA | AGA | GCA | TTG | ACT | CTA | 1265 |
|---|---|---|---|---|---|---|---|---|---|---|---|---|---|---|---|---|
| Gln | Trp | Ser | Ser | Val | Phe | Cys | Gly | Ile | Val | Ser | Arg | Ala | Leu | Thr | Leu | |
| 295 | | | | 300 | | | | | 305 | | | | | 310 | | |

| GAA | GTT | CTC | TCA | ACT | GGC | GTA | CGA | GGG | AAC | TAC | AAT | GGG | GCA | TTG | CAA | 1313 |
|---|---|---|---|---|---|---|---|---|---|---|---|---|---|---|---|---|
| Glu | Val | Leu | Ser | Thr | Gly | Val | Arg | Gly | Asn | Tyr | Asn | Gly | Ala | Leu | Gln | |
| | | | 315 | | | | | 320 | | | | | 325 | | | |

| GTG | ATG | ACA | GCA | GAG | TTC | CAA | GTC | CCA | TCG | CCG | CTT | GTC | CCT | ACT | CGT | 1361 |
|---|---|---|---|---|---|---|---|---|---|---|---|---|---|---|---|---|
| Val | Met | Thr | Ala | Glu | Phe | Gln | Val | Pro | Ser | Pro | Leu | Val | Pro | Thr | Arg | |
| | | | 330 | | | | | 335 | | | | | 340 | | | |

| GAG | AAC | TAC | TTT | GTA | AGG | TAC | TGT | AAA | CAG | CAC | AGT | GAC | GGT | ATT | TGG | 1409 |
|---|---|---|---|---|---|---|---|---|---|---|---|---|---|---|---|---|
| Glu | Asn | Tyr | Phe | Val | Arg | Tyr | Cys | Lys | Gln | His | Ser | Asp | Gly | Ile | Trp | |
| | | | 345 | | | | | 350 | | | | | 355 | | | |

| GCG | GTT | GTG | GAT | GTC | TCT | TTG | GAC | AGC | CTA | AGA | CCA | AGT | CCG | ATC | ACT | 1457 |
|---|---|---|---|---|---|---|---|---|---|---|---|---|---|---|---|---|
| Ala | Val | Val | Asp | Val | Ser | Leu | Asp | Ser | Leu | Arg | Pro | Ser | Pro | Ile | Thr | |
| | | | 360 | | | | | 365 | | | | | 370 | | | |

| AGA | AGC | AGA | AGA | AGA | CCC | TCT | GGT | TGT | CTG | ATT | CAA | GAA | TTG | CAG | AAT | 1505 |
|---|---|---|---|---|---|---|---|---|---|---|---|---|---|---|---|---|
| Arg | Ser | Arg | Arg | Arg | Pro | Ser | Gly | Cys | Leu | Ile | Gln | Glu | Leu | Gln | Asn | |
| 375 | | | | | 380 | | | | | 385 | | | | | 390 | |

| GGT | TAC | TCC | AAG | GTG | ACA | TGG | GTA | GAG | CAT | ATT | GAG | GTG | GAT | GAT | AGA | 1553 |
|---|---|---|---|---|---|---|---|---|---|---|---|---|---|---|---|---|
| Gly | Tyr | Ser | Lys | Val | Thr | Trp | Val | Glu | His | Ile | Glu | Val | Asp | Asp | Arg | |
| | | | | 395 | | | | | 400 | | | | | 405 | | |

| TCG | GTT | CAC | AAC | ATG | TAT | AAA | CCG | TTG | GTT | AAT | ACC | GGT | TTA | GCT | TTC | 1601 |
|---|---|---|---|---|---|---|---|---|---|---|---|---|---|---|---|---|
| Ser | Val | His | Asn | Met | Tyr | Lys | Pro | Leu | Val | Asn | Thr | Gly | Leu | Ala | Phe | |
| | | | 410 | | | | | 415 | | | | | 420 | | | |

| GGT | GCA | AAA | CGT | TGG | GTG | GCT | ACA | CTT | GAC | CGC | CAA | TGT | GAG | CGG | CTC | 1649 |
|---|---|---|---|---|---|---|---|---|---|---|---|---|---|---|---|---|
| Gly | Ala | Lys | Arg | Trp | Val | Ala | Thr | Leu | Asp | Arg | Gln | Cys | Glu | Arg | Leu | |
| | | 425 | | | | | 430 | | | | | 435 | | | | |

| GCC | AGT | TCC | ATG | GCC | AGC | AAC | ATT | CCG | GCT | TGT | GAT | CTT | TCC | GTG | ATA | 1697 |
|---|---|---|---|---|---|---|---|---|---|---|---|---|---|---|---|---|
| Ala | Ser | Ser | Met | Ala | Ser | Asn | Ile | Pro | Ala | Cys | Asp | Leu | Ser | Val | Ile | |
| 440 | | | | | 445 | | | | | 450 | | | | | | |

```
ACG AGT CCT GAG GGG AGA AAG AGC ATG CTG AAA CTA GCG GAG AGA ATG        1745
Thr Ser Pro Glu Gly Arg Lys Ser Met Leu Lys Leu Ala Glu Arg Met
455                 460                 465                 470

GTG ATG AGC TTC TGT ACC GGA GTC GGC GCG TCA ACC GCC GAT GCC TGG        1793
Val Met Ser Phe Cys Thr Gly Val Gly Ala Ser Thr Ala Asp Ala Trp
                475                 480                 485

ACT ACA TTG TCG ACC ACA GGA TCC GAC GAC GTT CGG GTC ATG ACC CGA        1841
Thr Thr Leu Ser Thr Thr Gly Ser Asp Asp Val Arg Val Met Thr Arg
            490                 495                 500

AAG AGC ATG GAT GAT CCG GGA AGA CCT CCA GGC ATC GTT CTC AGC GCC        1889
Lys Ser Met Asp Asp Pro Gly Arg Pro Pro Gly Ile Val Leu Ser Ala
        505                 510                 515

GCT ACT TCT TTC TGG ATC CCT GTA GCT CCA AAA CGA GTG TTC GAT TTT        1937
Ala Thr Ser Phe Trp Ile Pro Val Ala Pro Lys Arg Val Phe Asp Phe
    520                 525                 530

CTC AGA GAT GAA AAC TCA AGA AGC GAG TGG GAT ATA CTT TCC AAT GGA        1985
Leu Arg Asp Glu Asn Ser Arg Ser Glu Trp Asp Ile Leu Ser Asn Gly
535                 540                 545                 550

GGC TTG GTT CAA GAA ATG GCT CAT ATC GCA AAT GGT CGT GAT CCT GGG        2033
Gly Leu Val Gln Glu Met Ala His Ile Ala Asn Gly Arg Asp Pro Gly
                555                 560                 565

AAT AGT GTC TCC TTG CTT CGA GTC AAT AGT GGG AAC TCA GGG CAG AGC        2081
Asn Ser Val Ser Leu Leu Arg Val Asn Ser Gly Asn Ser Gly Gln Ser
                570                 575                 580

AAC ATG TTG ATC TTA CAA GAA AGT TGT ACG GAC GCA TCA GGG TCC TAT        2129
Asn Met Leu Ile Leu Gln Glu Ser Cys Thr Asp Ala Ser Gly Ser Tyr
            585                 590                 595

GTG ATA TAC GCA CCA GTT GAT ATA ATA GCT ATG AAC GTT GTC CTG AGT        2177
Val Ile Tyr Ala Pro Val Asp Ile Ile Ala Met Asn Val Val Leu Ser
        600                 605                 610

GGT GGT GAT CCG GAT TAT GTC GCT TTG TTA CCA TCC GGA TTC GCT ATT        2225
Gly Gly Asp Pro Asp Tyr Val Ala Leu Leu Pro Ser Gly Phe Ala Ile
615                 620                 625                 630

TTG CCG GAT GGC TCT GCT AGA GGA GGA GGA GGT AGT GCT AAT GCC AGT        2273
Leu Pro Asp Gly Ser Ala Arg Gly Gly Gly Gly Ser Ala Asn Ala Ser
                635                 640                 645

GCT GGA GCC GGA GTT GAA GGA GGA GGA GAG GGG AAT AAT CTT GAA GTG        2321
Ala Gly Ala Gly Val Glu Gly Gly Gly Glu Gly Asn Asn Leu Glu Val
                650                 655                 660

GTT ACT ACT ACT GGG AGT TGT GGC GGT TCA CTA CTC ACA GTT GCG TTT        2369
Val Thr Thr Thr Gly Ser Cys Gly Gly Ser Leu Leu Thr Val Ala Phe
            665                 670                 675

CAG ATA CTT GTT GAC TCT GTT CCT ACC GCT AAA CTC TCT CTC GGT TCA        2417
Gln Ile Leu Val Asp Ser Val Pro Thr Ala Lys Leu Ser Leu Gly Ser
        680                 685                 690

GTT GCT ACA GTC AAT AGT CTG ATC AAA TGC ACT GTC GAG CGG ATT AAA        2465
Val Ala Thr Val Asn Ser Leu Ile Lys Cys Thr Val Glu Arg Ile Lys
695                 700                 705                 710

GCC GCT CTG GCC TGC GAC GGA GCC TAATCGATGT TTTCGGAAGG TAAGAGTGAA       2519
Ala Ala Leu Ala Cys Asp Gly Ala
                715

AGGGGAGGTT TAGGGAGTTT ATGATAATGT TTGTGTTCTT TTGGTTTTTA AAGTCTTTTG      2579

AGATTCTCCA AAGGAAGTCA AGAACGCTCC TTTTTGCGTT TAATCTCATT TCCGCGTTTG      2639

TTAGCGGACG GGCCAAAGAA AGAGGCTTGA GAAAGAAAAG GTAAAGAGGT TCGGGTATTG      2699

ACTTCTGCTG GAACCAAAAA AAAAGGAATC GGGTTTGTTG TGTTTCGGCG GTTTAGCATT      2759

TTGCGTTTTC TTTGTTATTA TTTATCATTG ACTAGTGAAC AGTTTAGCGT TCTGCTTTTC      2819

GCGTCTACTG TGAAACTCCT TGTTATTAAG CCACTCTAGT GGTACTGTCA TTATATATTA      2879
```

TGAATCTATG AAACTGTGTT TATTAGTTTG TTTCTTTAAT CCAAACTTGA GATTCTCTTC  2939

(2) INFORMATION FOR SEQ ID NO:12:

(i) SEQUENCE CHARACTERISTICS:
        (A) LENGTH: 718 amino acids
        (B) TYPE: amino acid
        (D) TOPOLOGY: linear (ii) MOLECULE TYPE: protein (xi) SEQUENCE DESCRIPTION: SEQ ID NO:12:

```
Met Glu Asn Pro Leu Glu Glu Leu Gln Asp Pro Asn Gln Arg Pro
 1               5                  10                  15

Asn Lys Lys Lys Arg Tyr His Arg His Thr Gln Arg Gln Ile Gln Glu
                20                  25                  30

Leu Glu Ser Phe Phe Lys Glu Cys Pro His Pro Asp Asp Lys Gln Arg
            35                  40                  45

Lys Glu Leu Ser Arg Glu Leu Ser Leu Glu Pro Leu Gln Val Lys Phe
        50                  55                  60

Trp Phe Gln Asn Lys Arg Thr Gln Met Lys Ala Gln His Glu Arg His
65                  70                  75                  80

Glu Asn Gln Ile Leu Lys Ser Glu Asn Asp Lys Leu Arg Ala Glu Asn
                85                  90                  95

Asn Arg Tyr Lys Asp Ala Leu Ser Asn Ala Thr Cys Pro Asn Cys Gly
            100                 105                 110

Gly Pro Ala Ala Ile Gly Glu Met Ser Phe Asp Glu Gln His Leu Arg
        115                 120                 125

Ile Glu Asn Ala Arg Leu Arg Glu Glu Ile Asp Arg Ile Ser Ala Ile
130                 135                 140

Ala Ala Lys Tyr Val Gly Lys Pro Leu Met Ala Asn Ser Ser Ser Phe
145                 150                 155                 160

Pro Gln Leu Ser Ser Ser His His Ile Pro Ser Arg Ser Leu Asp Leu
                165                 170                 175

Glu Val Gly Asn Phe Gly Asn Asn Asn Ser His Thr Gly Phe Val
            180                 185                 190

Gly Glu Met Phe Gly Ser Ser Asp Ile Leu Arg Ser Val Ser Ile Pro
        195                 200                 205

Ser Glu Ala Asp Lys Pro Met Ile Val Glu Leu Ala Val Ala Ala Met
210                 215                 220

Glu Glu Leu Val Arg Met Ala Gln Thr Gly Asp Pro Leu Trp Val Ser
225                 230                 235                 240

Ser Asp Asn Ser Val Glu Ile Leu Asn Glu Glu Glu Tyr Phe Arg Thr
                245                 250                 255

Phe Pro Arg Gly Ile Gly Pro Lys Pro Ile Gly Leu Arg Ser Glu Ala
            260                 265                 270

Ser Arg Glu Ser Thr Val Val Ile Met Asn His Ile Asn Leu Ile Glu
        275                 280                 285

Ile Leu Met Asp Val Asn Gln Trp Ser Ser Val Phe Cys Gly Ile Val
290                 295                 300

Ser Arg Ala Leu Thr Leu Glu Val Leu Ser Thr Gly Val Arg Gly Asn
305                 310                 315                 320

Tyr Asn Gly Ala Leu Gln Val Met Thr Ala Glu Phe Gln Val Pro Ser
                325                 330                 335

Pro Leu Val Pro Thr Arg Glu Asn Tyr Phe Val Arg Tyr Cys Lys Gln
            340                 345                 350
```

```
His Ser Asp Gly Ile Trp Ala Val Val Asp Val Ser Leu Asp Ser Leu
        355                 360                 365

Arg Pro Ser Pro Ile Thr Arg Ser Arg Arg Pro Ser Gly Cys Leu
    370                 375                 380

Ile Gln Glu Leu Gln Asn Gly Tyr Ser Lys Val Thr Trp Val Glu His
385                 390                 395                 400

Ile Glu Val Asp Asp Arg Ser Val His Asn Met Tyr Lys Pro Leu Val
                405                 410                 415

Asn Thr Gly Leu Ala Phe Gly Ala Lys Arg Trp Val Ala Thr Leu Asp
            420                 425                 430

Arg Gln Cys Glu Arg Leu Ala Ser Ser Met Ala Ser Asn Ile Pro Ala
            435                 440                 445

Cys Asp Leu Ser Val Ile Thr Ser Pro Glu Gly Arg Lys Ser Met Leu
450                 455                 460

Lys Leu Ala Glu Arg Met Val Met Ser Phe Cys Thr Gly Val Gly Ala
465                 470                 475                 480

Ser Thr Ala Asp Ala Trp Thr Thr Leu Ser Thr Thr Gly Ser Asp Asp
                485                 490                 495

Val Arg Val Met Thr Arg Lys Ser Met Asp Asp Pro Gly Arg Pro Pro
                500                 505                 510

Gly Ile Val Leu Ser Ala Ala Thr Ser Phe Trp Ile Pro Val Ala Pro
            515                 520                 525

Lys Arg Val Phe Asp Phe Leu Arg Asp Glu Asn Ser Arg Ser Glu Trp
            530                 535                 540

Asp Ile Leu Ser Asn Gly Gly Leu Val Gln Glu Met Ala His Ile Ala
545                 550                 555                 560

Asn Gly Arg Asp Pro Gly Asn Ser Val Ser Leu Leu Arg Val Asn Ser
                565                 570                 575

Gly Asn Ser Gly Gln Ser Asn Met Leu Ile Leu Gln Glu Ser Cys Thr
            580                 585                 590

Asp Ala Ser Gly Ser Tyr Val Ile Tyr Ala Pro Val Asp Ile Ile Ala
            595                 600                 605

Met Asn Val Val Leu Ser Gly Gly Asp Pro Asp Tyr Val Ala Leu Leu
            610                 615                 620

Pro Ser Gly Phe Ala Ile Leu Pro Asp Gly Ser Ala Arg Gly Gly Gly
625                 630                 635                 640

Gly Ser Ala Asn Ala Ser Ala Gly Ala Gly Val Glu Gly Gly Gly Glu
                645                 650                 655

Gly Asn Asn Leu Glu Val Val Thr Thr Thr Gly Ser Cys Gly Gly Ser
            660                 665                 670

Leu Leu Thr Val Ala Phe Gln Ile Leu Val Asp Ser Val Pro Thr Ala
            675                 680                 685

Lys Leu Ser Leu Gly Ser Val Ala Thr Val Asn Ser Leu Ile Lys Cys
690                 695                 700

Thr Val Glu Arg Ile Lys Ala Ala Leu Ala Cys Asp Gly Ala
705                 710                 715
```

(2) INFORMATION FOR SEQ ID NO:13:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide

```
    (ix) FEATURE:
          (A) NAME/KEY: Modified-site
          (B) LOCATION: one-of(2, 3, 5, 6, 7, 9, 10)
          (D) OTHER INFORMATION: /product= "OTHER"
                /note= "Xaa = non-conserved amino acid
                residue in cytochrome P450 motif
                linking heme group to polypeptide
                through cysteine residue in position 8"

(xi) SEQUENCE DESCRIPTION: SEQ ID NO:13:

Phe Xaa Xaa Gly Xaa Xaa Xaa Cys Xaa Xaa Gly
1               5                   10
```